United States Patent [19]

Arnould et al.

[11] Patent Number: 5,013,730
[45] Date of Patent: May 7, 1991

[54] CEPHEM DERIVATIVES

[75] Inventors: Jean C. Arnould, Cormontreuil; Thomas G. C. Bird, Witry-Les-Reims, both of France

[73] Assignee: ICI-PHARMA, Gergy Cedex, France

[21] Appl. No.: 219,779

[22] Filed: Jul. 18, 1988

[30] Foreign Application Priority Data

Jul. 23, 1987 [EP] European Pat. Off. .......... 87401720

[51] Int. Cl.$^5$ ............... C07D 501/38; A61K 31/545
[52] U.S. Cl. ..................................... 514/202; 540/222; 540/225; 540/221; 514/201
[58] Field of Search ................. 540/221, 222, 225; 514/202

[56] References Cited

U.S. PATENT DOCUMENTS 4,278,793 7/1981 Durckheimer ............... 544/027
4,678,781 7/1987 Jung ..................... 540/227

FOREIGN PATENT DOCUMENTS 182210 5/1986 European Pat. Off. .
186187 7/1987 European Pat. Off. .
238060 8/1987 European Pat. Off. .
241901 10/1987 European Pat. Off. .
1399086 6/1975 United Kingdom .

Primary Examiner—Nicholas S. Rizzo
Attorney, Agent, or Firm—Cushman, Darby & Cushman

[57] ABSTRACT

Cephalosporins having a 3-position substituent of the formula:

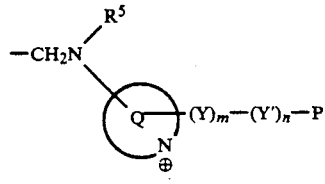

are described, wherein $R^5$ is hydrogen, alkenyl, alkyl or substituted alkyl, Q is a mono- or bicyclic heterocyclic ring, variously substituted, Y is variously substituted alkylene, Y' represents various linking groups, m and n are independently zero or one, and P is a benzene ring with two ortho groups, one of which is hydroxy or an in-vivo hydrolysable ester thereof and the other is hydroxy, an in vivo hydrolysable ester thereof, carboxy, sulpho, hydroxymethyl, —NHSO$_2$CH$_3$ or —NHCONH$_2$; or P is a particularly substituted pyridone or pyranone. The use of such compounds as antibacterial agents is described, as are processes for their preparation.

8 Claims, No Drawings

CEPHEM DERIVATIVES

This invention relates to cephalosporin derivatives which have antibacterial activity In this specification (including in the claims) the term "cephalosporin derivative", irrespective of the actual derivation of any individual such compound, includes the cephalosporins and the 7α-methoxy, 7α-formamido and 1-oxide derivatives thereof (wherein the 1-oxides may have the R or S configuration) and analogues of the above compounds wherein the sulphur atom or sulphinyl group at the 1-position is replaced by an oxygen atom or a methylene group.

The cephalosporin derivatives referred herein are generally named in accordance with the "cephem" nomenclature and numbering system proposed in J. Amer. Chem. Soc. 1962, 84, 3400.

Formulae referred to by roman numerals are set out hereinafter.

According to the invention there is provided a cephalosporin derivative having antibacterial activity characterised in that the substituent at the 3-position has the formula I in which:

R5 is hydrogen, (1-4C)alkyl, halo(1-4C)alkyl, hydroxy(1-4C)alkyl, (1-4C)alkoxy(1-4C)alkyl, carboxy(1-4C)alkyl, amino(1-4C)alkyl, cyano(1-4C)alkyl, (1-4C) alkanoylamino(1-4C)alkyl, (3-6C)alkenyl, phenyl(1-4C)alkyl or heteroaryl (1-4C) alkyl wherein heteroaryl is a 5- or 6-membered ring containing 1,2 or 3-heteroatoms selected from nitrogen, oxygen and sulphur;

Q represents a 5 to 10-membered mono- or bicyclic heterocyclic ring system bonded to NR5 via a carbon atom and containing, in addition to the positively charged nitrogen atom, 0 to 5 further heteroatoms selected from nitrogen, oxygen and sulphur and being optionally substituted:

on a carbon atom or atoms available for substitution by 1,2 or 3 groups R26 wherein R26 is halogen, (1-6C)alkyl, carboxy, (2-6C)alkoxycarbonyl, (2-6C) alkoxycarbonyl(1-4C)alkyl, (1-6C)alkoxy, (1-6C)alkylthio, cyano, (1-4C) cyanoalkyl, amino, (1-6C)alkylamino, (2-8C)dialkylamino, phenyl(1-4C)alkylamino, nitrophenyl(1-4C)alkylamino, heteroaryl(1-4C)alkylamino (wherein heteroaryl is as hereinbefore defined), (3-6C)alkenylamino, amino(1-6C)alkylamino, (1-6C)alkoxy(1-6C)alkylamino, hydroxy(1-6C)alkylamino, hydroxy, mercapto, carbamoyl, (2-6C)alkylcarbamoyl, (3-10C)dialkylcarbamoyl, phenylthio and heteroarylthio (wherein heteroaryl is as hereinbefore defined), wherein when more than one group R26 is present these may be the same or different;

on an uncharged nitrogen atom available for substitution by a group R27 wherein R27 is (1-6C)alkyl, phenyl or benzyl;

on the charged nitrogen atom where possible by a group R30 wherein R30 is hydrogen, (1-6C)alkyl (optionally substituted by carboxy, (1-6C)alkoxycarbonyl, carbamoyl, mono-or di-(1-4C)alkylcarbamoyl, hydroxy, (1-4C)alkoxy, amino, mono-or di-(1-4C)alkylamino, (1-4C)alkanoyl, benzoyl, cyano, carboxyaminocarbonyl, (1-6C)alkoxycarbonylaminocarbonyl, (1-4C)alkoxy(2-4C)alkoxy or phenyl), (1-6C)alkoxy, phenyl(1-6C)alkoxy, amino, (1-6C)alkylamino, (3 6C)cycloalkyl, (3 6C)cycloalkenyl, cyano(3 6C)cycloalkenyl, (2-6C)alkenyl (optionally substituted by (1-6C)alkyl, halogen, cyano, carbamoyl, mono- or di(1-4C)alkylcarbamoyl, piperidinocarbonyl or morpholinocarbonyl), 2-ureidoethyl, 2-thioureidoethyl, 2-(thioacetylamino)ethyl, sulphamoyl, 2-amino-2-carboxyethyl, acetylaminomethyl, phthalimidomethyl, 4-5-dihydroimidazol-2-yl-methyl, 3,4,5,6-tetrahydropyrimidin-2-ylmethyl, 2-(1,2,3,6-tetrahydro-2,6-dioxopurin-7-yl)ethyl, 2-hydroxyiminopropyl (syn or anti) [(1-4C)alkoxyimino]propyl (syn or anti) or phenyl, or R30 is of the formula $-(CH_2)_2-NR31R32R33$ in which R31, R32 and R33 are (1-4C)alkyl, or R30 is of the formula $-(CH_2)_s$-R34 in which s is 0-2 and R34 is pyridine, pyridazine, pyrimidine, pyrazine, 1,2,5,6-dihydro-5,6-dioxo-1,2,4-triazine, 2-[(1-4C)alkyl]-1,2,5,6-dihydro-5,6-dioxo-1,2,4-triazine, 1-[(1-4C) alkyl]tetrazole, furan, thiophene, pyrrole, 1-[(1-4C)alkyl]-pyrrole, oxazole, thiazole, imidazole, 1-[1-4C)alkyl]imidazole, isoxazole, isothiazole, pyrazole, 1,2,3-thiadiazole, 1-[(1-4C)alkyl]pyrazole, benzfuran, benzthiophene, indole, oxindole, 1-[(1-4C)alkyl]indole, benzoxazole, benzthiazole, benzimidazole, 1-(1-4C)alkyl]benzimidazole, or 3,4-dihydro-4-oxo-2H-benzo[e]oxazine (each of these ring systems being linked to $(CH_2)_s$ through carbon and each ring system being optionally substituted by halogen, (1-6C)alkyl, (1-4C)haloalkyl, (3-6C) cycloalkyl, (3-6C)cycloalkyl(1-4C)alkyl, (2-6C)alkenyl, carboxy, (2-6C)alkoxycarbonyl, (1-6C)alkoxy, cyano, (2-6C) cyanoalkenyl, carbamoyl, mono-or di-(1-4C)alkylcarbamoyl, (1-4C)alkanoylamino, guanidino, hydroxy, nitro or amino), or R30 is 2-guanidino-thiazol-4-ylmethyl, hydroxybenzoylmethyl, 2-thenyl, 2-imidazolylmethyl or cinnamyl (each optionally substituted by halogen, (1-6C)alkyl, hydroxy, (1-4C)alkoxy, carboxy, (2-6C)alkoxycarbonyl, nitro or carbamoyl), or R30 is $-(CH_2)_tNHCOR35$ or $-(CH_2)_t-S(O)_u-R35$ in which t is 1-6, u is 0, 1 or 2 and R35 is (1-6C)alkyl or (1-6C)alkoxy, or R30 is of the formula $(CH_2)_2N=CR36NR37R38$ or $-(CH_2)_vC(=NR36)NR37R38$ or a tautomer thereof in which v is 1-6 and R36, R37, R38 are hydrogen or (1-4C)alkyl, (wherein when R30 is or contains a phenyl group, the phenyl group is optionally substituted by 1 or 2 groups selected from halogen, (1-6C)alkyl, (1-6C)alkoxy, amino, carboxy, nitro, carbamoyl, cyano, trifluoromethyl, aminomethyl, (1-4C)alkanoyl, (1-4C)alkanoylamino, halo(1-4C)alkyl, (2-6C)alkoxycarbonyl, mono- or di-(1-4C)alkylcarbamoyl, mesyl, vinyl, sulpho, sulphamoyl or mono- or di(1-4C)alkylsulphamoyl);

Y is straight or branched (1-6C)alkylene optionally substituted by cyano, carboxy, (1-4C)alkoxycarbonyl, nitro, halogen, carbamoyl, mono-or di(1-4C)alkylcarbamoyl or trifluoromethyl;

Y' is $-CO-$, $-NHCO-$, $-CONH-$, $-NHSO_2-$, $-SO_2NH-$, $-O-$, $-S-$, $-CH=CH-$ or $-NR^a-$ wherein $R^a$ is hydrogen, (1-4C)alkyl or (2-4C) alkenyl;

m and n are each 0 or 1, the link between ring Q and the group $-(Y)_m-(Y')_n-P$ being via an available site on ring Q selected from the positively charged nitrogen atom, an uncharged nitrogen atom or a carbon atom such that when m=0 and n=0 the rings Q and P are linked directly by a covalent bond or are fused on available carboncarbon or carbon-nitrogen bonds;

P represents:

(i) a benzene ring optionally fused to a further benzene ring (so forming a naphthyl group) or to a 5 or 6 membered heterocyclic aromatic group containing 1, 2 or 3 heteroatoms selected from nitrogen, oxygen and sulphur and said ring system substituted by groups W and Z which are ortho with respect to one another wherein W is hydroxy or an in vivo hydrolysable ester thereof and Z is hydroxy, an in vivo hydrolysable ester thereof, carboxy, sulpho, hydroxymethyl, —NHSO$_2$CH$_3$, or —NHCONH$_2$;

(ii) a group of formula II; or (iii) a group of formula III and tautomers thereof wherein M represents oxygen or NR$^b$ wherein R$^b$ represents hydrogen or (1–4C) alkyl, ring system P optionally being further substituted by (1–4C)alkyl, halogen, hydroxy, cyano, trifluoromethyl, nitro, amino, mono- or di-(1–4C)alkylamino, formyl, (1–4C)alkanoyl, (1–4C)alkoxy, (1–4C)alkylthio, (1–4C)alkanoyloxy, carbamoyl or mono- or di(1–4C)alkylcarbamoyl;

and the N-oxides thereof where chemically possible;

and the salts formed with acids and bases which afford pharmaceutically acceptable anions and cations respectively.

A particular group of compounds according to the invention are those of formula Ia and salts thereof wherein R5, Q, Y, Y', m, n and P are as hereinbefore defined and in which X is sulphur, oxygen, methylene or sulphinyl (R or S configuration) and R1, R$^4$ and A are groups known in the art of antibacterial cephalosporins R1 is for example 2-aminothiazol-4-yl or 2-aminooxazol-4-yl each optionally substituted in the 5-position by fluorine, chlorine or bromine, or R1 is 5-aminoisothiazol-3-yl, 5-amino-1,2,4-thiadiazol-3-yl, 3-aminopyrazol-5-yl, 3-aminopyrazol-4-yl, 2-aminopyrimidin-5-yl, 2-aminopyrid-6-yl, 4-aminopyrimidin-2-yl, 2-amino-1,3,4-thiadiazol-5-yl or 5-amino-1-methyl-1,2,4-triazol-3-yl.

A is for example of the formula =N.O. R2 (having the syn configuration about the double bond) wherein R2 is hydrogen, (1–6C)alkyl, (3–8C)cycloalkyl, (1–3C)alkyl(3–6C)cycloalkyl, (3–6C)cycloalkyl(1–3C)alkyl, (3–6C)alkenyl, optionally substituted by carboxy, (5–8C)cycloalkenyl, (3–6C) alkynyl, (2–5C)alkylcarbamoyl, phenylcarbamoyl, benzylcarbamoyl, di-(104C}-alkylcarbamoyl(1–4C)alkyl, (1–4C)haloalkylcarbamoyl(1–4C)alkyl, (1–3C) haloalkyl, (2–6C) hydroxyalkyl, (1–4C)alkoxy(2–4C)alkyl, (1–4C)alkylthio(2–4C)alkyl, (1–4C)alkanesulphinyl(1–4C)alkyl, (1–4C)alkanesulphonyl(1–4C)alkyl, amino(2–6C)alkyl, azido(2–6C)alkyl, ureido(C$_{2-6}$)alkyl,(1–4C)alkylamino(1–6C)alkyl, (2–8C)dialkyllino(2–6C)alkyl, (1–5C)cyanoalkyl, 3-amino-3-carboxypropyl, 2-(amsidino)ethyl, 2-(amidinothio)ethyl, 2-(N aminoamidinothio)ethyl, tetrahydropyran-2-yl, thietan-3-yl, 2-oxopyrrolidinyl, or 2-oxotetrahydrofuranyl, or —R2 is of the formula IV in which q is 1 or 2 and R14 and R15 are hydrogen or (1–4C)alkyl, or —R2 is of the formula V in which r is 0–3, R22 is hydrogen, (1–3C)alkyl or methylthio, R23 is hydrogen, (1–3C)alkyl, (3–7C)cycloalkyl, cyano, carboxy, (2–5C)carboxyalkyl or methanesulphonylamino, or R22 and R23 are joined to form, together with the carbon to which they are attached, a (3–7C)-carbocyclic ring, and R24 is hydroxy, amino, (1–4C)alkoxy, (1–4C) alkylamino or of the formula NHOR25 in which R25 is hydrogen or (1–4C)alkyl:

or A may be of the formula =CH.R3 wherein R3 is hydrogen, halogen, (1–6C)alkyl, (3–7C)cycloalkyl, (2–6C)alkenyl, (3–7C)cycloalkenyl, phenyl or benzyl.

R4 is suitably hydrogen, methoxy or formamido.

It is to be understood that in the above formula I and throughout this specification, the illustrated stereochemistry of the ceph-3-em nucleus, and its optional modifications at the 1-position, is the absolute configuration. It is also to be understood that, since ring Q contains a quaternary nitrogen, the compounds of formula I will normally exist in zwitterionic form, involving the quaternary nitrogen and the carboxy group. When the compound of the formula I contains further acidic or basic substituents, it is to be understood that the possibility of a double zwitterionic form of the compound will arise. Alternatively, exogenous anions or cations may be included, to form pharmaceutically-acceptable base-addition or acid-addition salts, as defined above.

It will also be understood that references herein to a particular nitrogen atom bearing a positive charge and to other nitrogen atoms being uncharged are made for the sake of convenience in defining the compounds of the invention and that all possible resonance hybrids of the structures so defined are included within the scope of the invention.

A particular meaning for R2 is hydrogen, methyl, ethyl, isopropyl, t-butyl, cyclopropyl, cyclobutyl, cyclopentyl, cyclohexyl, methylcyclopropyl, methylcyclobutyl, methylcyclopentyl, methylcyclohexyl, cyclopropylmethyl, cyclobutylmethyl, cyclopentylmethyl, allyl, cyclopentenyl, cyclohexenyl, propargyl, methylcarbamoyl, ethylcarbamoyl, phenylcarbamoyl, benzylcarbamoyl, 2-chloroethyl, 2-fluoroethyl, 2-bromoethyl, 2-hydroxyethyl, 3-hydroxypropyl, 2-methoxyethyl, 2-ethoxyethyl, 2-methylthio-ethyl, 2-methanesulphinylethyl, 2-methanesulphonyl-ethyl, 2-aminoethyl, 3-aminopropyl, 2-methylaminoethyl, 2-dimethylaminoethyl, cyanomethyl, 2-cyanoethyl, azidomethyl, 2-azidoethyl, ureidomethyl, 3-amino-3-carboxypropyl, 2-(amidino)ethyl, 2-(N-aminoamidino)-ethyl, tetrahydropyran-2-yl, thietan-3-yl, 2-oxopyrrolidinyl or 2-oxotetrahydrofuran-3-yl, or, when R2 is of the formula IV in which q is 1 or 2, a particular meaning for R2 is when R14 and R15 are hydrogen or methyl, or, when R2 is of the formula V, a particular meaning for R2 is when r=O and R22 is hydrogen, methyl or methylthio, R23 is hydrogen, methyl, cyclopropyl, cyclobutyl, cyclopentyl, cyclohexyl, cyano, carboxy, carboxymethyl, 2 carboxyethyl or methanesulphonylamino, or when R22 and R23 are joined to form, together with the carbon to which they are attached, a cyclopropane, cyclobutane, cyclopentane, cyclohexane or cycloheptane ring and R24 is hydroxy, amino, methoxy, ethoxy, methylamino, ethylamino, or of the formula NHOR25 in which R25 is hydrogen, methyl or ethyl.

Preferably R$^2$ is C$_{1-6}$alkyl for example methyl or ethyl, 1-carboxycyclobutyl, 1-carboxycyclophentyl, or 2 carboxyprop-2-yl.

Particular meanings for R3 are hydrogen, methyl or chlorine.

A particular meaning for R4 is hydrogen.

Particular meanings for R5 are hydrogen, methyl, ethyl, n-propyl, isopropyl, 2-fluoroethyl, 2-chloroethyl 2-bydroxymethyl, 2-methoxyethyl, carboxymethyl, (R) and (S) 1-carboxyethyl, 2-aminoethyl, 2-cyanoethyl, 2-formamidoethyl, allyl, furfuryl, benzyl or 4-pyridylmethyl.

A particular ring system represented by ring Q is a 5 or 6 membered ring containing the positively charged nitrogen atom and 0 to 3 further heteroatoms selected from nitrogen, oxygen and sulphur optionally fused on an available carbon-carbon or carbon-nitrogen bond to a benzene ring or a ring of formula (VI) wherein T, U and V are selected from oxygen, sulphur, nitrogen, carbon, —NH— and —CH—, and optionally substituted, where possible, by one or more groups R26, R27 and R30 as hereinbefore defined Further particular ring systems represented by ring Q are those of formulae VII–XIV wherein D,D', E and E' represent nitrogen atoms, one of which bears the positive charge.

Still further particular ring systems represented by ring Q are those of formula XV and XVI wherein R29 represents hydrogen or a group R27 as hereinbefore defined, and XVII–XXI.

Still further particular ring systems represented by ring Q are those of formulae XXII (wherein T is as hereinbefore defined) and XXIII–XXVI.

It will be understood that in formulae VII–XXVI $(Y)_m$ (or when m=0, $(Y')_n$, or when m=0 and n=0, ring P) may be linked to an available site on ring Q selected from the positively charged nitrogen atom, an uncharged nitrogen atom having a valency available for substitution or a carbon atom, or (when m=0 and n=0) rings Q and P may be fused on available carbon-carbon or carbon nitrogen bonds.

It will similarly be understood that in formulae XXII–XXVI $(Y)_m$ (or when m=0, $(Y')_n$, or when m=0 and n=0, ring P) is linked to a carbon atom of ring Q or the rings Q and P are fused.

Any of rings VII–XXVI may optionally be substituted where possible, by one or more groups R26, R27 and R30 as hereinbefore defined.

When ring Q represents a 5-or 6-membered ring as defined above a particular meaning therefor is pyridine or pyrimidine optionally fused to a benzene ring or a ring of formula VI which is a thienyl group.

Particular meanings for the group R26 are fluorine, chlorine, bromine, methyl, ethyl, n-propyl, isopropyl, carboxy, methoxycarbonyl, ethoxycarbonyl, methoxycarbonylmethyl, ethoxycarbonylmethyl, methoxy, ethoxy, methylthio, ethylthio, cyano, cyanomethyl, 2-cyanoethyl, amino, methylamino, ethylamino, isopropylamino, dimethylamino, benzylamino, nitrobenzylamino, allylamino, 2-aminoethylamino, 2-methoxyethylamino, 2-hydroxy ethylamino, hydroxy, mercapto, carbamoyl, methylcarbamoyl, ethylcarbamoyl, dimethylcarbamoyl, phenylthio and heteroarylthio in which the heteroaryl ring is a furan, thiophene, imidazole, thiazole, pyrazole, thiadiazole, pyridine, pyrimidine, pyrazine or pyridazine.

Particular meanings for the group R27 are methyl, ethyl, n-propyl, isopropyl, phenyl or benzyl.

Particular meanings for R29 are hydrogen and the particular meanings given above for R27.

Particular meanings for the group R30 are hydrogen, methyl, ethyl, n-propyl, isopropyl, t-butyl, carboxymethyl, 2-carboxyethyl, methoxycarbonylmethyl, 2-methoxycarbonylethyl, carbamoylmethyl, 2-carbamoylethyl, mono-and dimethylcarbamoylmethyl, hydroxymethyl, 2-hydroxyethyl, methoxymethyl, 2-methoxyethyl, aminomethyl, 2-aminoethyl, 2-methylaminoethyl, 2-dimethylaminoethyl, acetylmethyl, propionylmethyl, benzoylmethyl, cyanomethyl, 2-cyanoethyl, 3-cyanopropyl, carboxyaminocarbonylmethyl, 2-(carboxyaminocarbonyl)ethyl, methoxycarbonylaminocarbonylmethyl, 2-(methoxycarbonylaminocarbonyl)ethyl, 2-methoxyethoxymethyl, benzyl, 2-phenethyl, methoxy, ethoxy, benzyloxy, 2-phenylethoxy, amino, methylamino, ethylamino, cyclopropyl, cyclobutyl, cyclopentyl, cyclopentenyl, 3-cyanocyclopent-2-enyl, vinyl, allyl, 2,4-pentadienyl, 3-chloroallyl (cis and trans), 3-cyanoallyl, 2-ureidoethyl, 2-thioureidoethyl, 2-thioacetylamino)ethyl, sulphamoyl, 2-amino- 2-carboxyethyl, acetylaminomethyl, phthalimidomethyl, 4,5-dihydroimidazol-2-ylmethyl, 3,4,5,6-tetrahydropyrimidin-2-ylmethyl, 2-(1,2,3,6-tetrahydro-2,6-dioxopurin-7-yl) ethyl, 2-hydroxyiminopropyl (syn or anti), 2-(methoxyimino)propyl (syn or anti), 2-(ethoxyimino)propyl (syn or anti) or phenyl, or where R30 is of the formula —(CH$_2$)$_2$—NR31R32R33 in which R31, R32 and R33 are methyl or ethyl, or where R30 is of the formula —(CH$_2$)s-R34 in which s is 0–2 and R34 is pyridine, pyridazine, pyrimidine, pyrazine, 1,2,5,6-dihydro-5,6-dioxo-1,2,4-triazine, 2-(methyl or ethyl) 1,2,5,6-dihydro-5,6-dioxo-1,2,4-triazine, 1-(methyl or ethyl)tetrazole, furan, thiophene, pyrrole, 1-(methyl or ethyl)pyrrole, oxazole, thiazole, imidazole, 1-(methyl or ethyl)imidazole, isoxazole, isothiazole, pyrazole, 1-(methyl or ethyl) pyrazole, 1,2,3-thiadiazole, benzfuran, benzthiophene, indole, 1-(methyl or ethyl)indole, oxindole, benzoxazole, benzthiazole, benzimidazole, 3,4-dihydro-4-oxo-2H-benzo[e]oxazine, 1-(methyl or ethyl)benzimidazole, each of these ring systems being linked to (CH$_2$)$_s$ through carbon and each ring system being optionally substituted by fluorine, chlorine, bromine, methyl, ethyl, n-propyl, isopropyl, trifluoromethyl, cyclopropylmethyl, formamido, carboxy, methoxycarbonyl, ethoxycarbonyl, methoxy, ethoxy, cyano, 3-cyanoallyl, carbamoyl, methylcarbamoyl, dimethylcarbamoyl, hydroxy, guanidino, nitro or amino, or where R30 is 2-guanidinothiazol-4-ylmethyl, 3-hydroxybenzoylmethyl, 2-thenyl, 2-imidazolymethyl or cinnamyl, each optionally substituted by fluorine, chlorine, bromine, methyl, ethyl, n-propyl, isopropyl, hydroxy, methoxy, ethoxy, carboxy, methoxycarbonyl, ethoxycarbonyl or carbamoyl, or where R30 is of the formula —(CH$_2$)$_t$—NH—CO—R35 or (CH$_2$)$_r$-S (O)$_s$-R35 in which t is 1–6, s is 0, 1 or 2 and R35 is methyl, ethyl, methoxy or ethoxy, or where R30 is of the formula (CH$_2$)$_2$N=CR36NR37R38 or (CH$_2$)$_2$C(=NR36)NR37R38 in which R36, R37 and R38 are hydrogen or methyl, (wherein when R30 is or contains a phenyl group the phenyl group is optionally substituted by 1 or 2 groups selected from fluorine, chlorine, bromine, amino, carboxy, nitro, carbamoyl, cyano, trifluoromethyl, aminomethyl, methyl, ethyl, methoxy, ethoxy, acetyl, acetamido, methoxycarbonyl, ethoxycarbonyl, methylcarbamoyl, dimethylcarbamoyl, mesyl and sulpho).

Particular meanings of Y include $C_{1-6}$ alkylene for example methylene (—CH$_2$—), ethylene (—CH$_2$CH$_2$—) and propylene (—CH$_2$CH$_2$CH$_2$—). A particular meaning of Y' is —NHCO—. Preferably —(Y)$_m$—(Y')$_n$— represents methylene, ethylene, —CH$_2$CH$_2$NHCO— or both m and n are zero so that rings Q and P are linked directly by a covalent bond. In another preferred aspect m and n are both zero and the rings Q and P are fused on available carbon-carbon or carbon-nitrogen bonds, for example ring Q is a pyrimidine or pyridine ring having fused thereto a benzene ring, said benzene bearing groups W and Z as hereinbefore defined. In particular the ring system formed by the fused rings Q and P is quinoline or quinazoline.

Preferably P is a benzene ring substituted by groups W and Z and optionally further substituted by halo for example bromo. W is hydroxy or an in-vivo hydrolysable ester thereof. In-vivo hydrolysable esters are those pharmaceutically acceptable esters that hydrolyse in the human or animal body to produce the parent hydroxy compound. Such esters can be identified by administering e.g. intravenously to a test animal the compound under test and subsequently examining the test animal's body fluids. Suitable in-vivo hydrolysable esters include $C_{1-6}$ alkanoyloxy for example acetoxy, propionyloxy, pivaloyloxy, $C_{1-4}$alkoxycarbonyloxy for example ethoxycarbonyloxy, and phthalidyloxy. Preferably Z is hydroxy or an in-vivo hydrolysable ester thereof. Conveniently W and Z have the same value and are both hydroxy or both in-vivo hydrolysable esters, for example they are both acetoxy or pivaloyoxy.

A particular acid which affords a pharmaceutically-acceptable anion is, for example, hydrochloric, hydrobromic, phosphoric, sulphuric, citric or maleic acid.

A particular base which affords a pharmaceutically acceptable cation is, for example, a base containing an alkali metal, (e.g. sodium or potassium) or an alkaline earth metal (e.g. calcium or magnesium), or a primary, secondary or tertiary organic amine (e.g. triethylamine, morpholine, N-methylpiperidine, N-ethylpiperidine, procaine, dibenzylamine or N,N'-dibenzylethylenediamine), or other amine which has been used to form salts with cephalosporins.

The compounds of formula I may be prepared by the following processes, which form further aspects of the invention, and in which R1, A, R2, R3, R4, R5, Q, P, m, n, X, Y and Y' have the meanings already assigned to them.

(A) Reaction of a cephalosporin derivative having a group of formula —CH₂L (wherein L is a leaving group) at the 3-position with a nucleophilic compound serving to form the group of formula I.

A nucleophilic compound serving to form the compound of formula I may be for example a compound of formula XXVII or XXVIII. Particular meaning for the leaving group L include $C_{1-4}$alkanoyloxy (e.g. acetoxy) and halo (e.g. chloro or iodo).

(B) Reaction of a cephalosporin derivative having a group —CH₂NHR5 at the 3-position with a compound of formula XXIX (wherein R39 is a leaving group)

Particular meanings for the leaving group R39 include (1–4C)alkylthio (eg methylthio), (1–4C)alkylsulphoxy (eg methylsulphoxy) and halogen (eg chlorine).

(C) Reaction of a cephalosporin derivative having a group of formula XXX at the 3-position with a compound of formula XXXI wherein J and K in the above formulae XXX and XXXI are such that reaction takes place to form the link —(Y)$_m$—(Y')$_n$— between the rings Q and P.

Particular meanings for J and K include for example where J represents —(CH₂)$_{1-6}$NH₂ and K represents —COCl or —COOH which react to form a link —(Y)$_m$—(Y')$_n$— of formula —(CH₂)$_{1-6}$—NHCO—.

(D) (Where a compound in which W and Z are hydroxy groups is desired) deprotection of a corresponding compound in which hydroxy groups W and Z are protected by hydroxyl protecting groups.

(E) (Where a compound in which W and Z are in-vivo hydrolysable ester groups is required) reaction of a compound in which W and Z are hydroxy groups with an appropriate acid or a reactive derivative thereof. Particular in-vivo hydrolysable ester groups are (1–4C)alkanoyloxy groups. A reactive derivative of a (1–4C)alkanoic acid may be for example the acid chloride.

(F) (Where a compound of formula I having a free carboxy group is required) deprotection of a corresponding compound containing a protected carboxy group.

(G) (Where a salt of the compound of formula I is required) reaction of a compound of formula I having a free acidic or basic group with a pharmaceutically acceptable base or acid.

(H) (Where a compound of formula I having a free amino group is required) deprotection of a corresponding compound having a protected amino group.

(I) (Where a compound of formula I which is a 1-oxide is required) oxidation of the corresponding 1-S compound by conventional means.

(J) (Where a compound of formula I having S at the 1-position is required) reduction of the corresponding 1-oxide by conventional means.

(K) Introduction or modification of a group at the 7-position of the cephalosporin derivative. For example, a compound of formula Ia may be prepared by one of the following processes:

(K)(a) Reaction of a compound of formula XXXII with an acid of formula XXXIII or a reactive derivative thereof.

(K)(b) Reaction of a compound of formula XXXIV with a compound of formula R2—O—NH₂.

(K)(c) (Where a compound of formula Ia wherein R2 is other than hydrogen is required) reaction of a compound of formula Ia wherein R2 is hydrogen with a compound of formula R40-R41 wherein R40 is a leaving group and R41 has one of the meanings given for R2 other than hydrogen.

(K)(d) Formation of a group R1 by cyclisation of an appropriate precursor therefor.

For example a 2-aminothiazol-4-yl group may be formed by reacting a compound of formula XXXV (wherein R42 is a leaving group) with a compound of formula XXXVI (wherein R43 is amino or protected amino) followed by removal of the amino protecting group if present.

Certain cephalosporin compounds used as starting materials in the preparation of the compounds of the present invention are described in our published European Patent Applications Nos. 127992 and 164944, or may be prepared by methods analogous to those described in the said applications.

In a further aspect the invention provides, as starting materials for the manufacture of antibacterial compounds of formula I, the following novel compounds as defined above:

1. A compound of formula XXXII and derivatives thereof wherein the 7-amino group is protected;
2. A compound of formula XXXIV;
3. A compound of formula XXXV.

When reference is made to protecting groups being present at any position in the compounds described herein such protecting groups may in general be chosen from any of the groups described in the literature or known to the skilled chemist as appropriate for the protection of the group in question, and may be introduced by conventional methods.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower" signifies that the group to which it is applied preferably has 1–4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxyl protecting group may be the residue of an ester-forming aliphatic or araliphatic alcohol or of an ester-forming phenol silanol or stannanol (the said alcohol, phenol, silanol or stannanol preferably containing 1–20 carbon atoms).

Examples of carboxyl protecting groups include straight or branched chain (1–12C)alkyl groups (eg isopropyl, t-butyl); halo lower alkyl groups (eg 2-iodoethyl, 2,2,2-trichloroethyl); lower alkoxy lower alkyl groups (eg methoxymethyl, ethoxymethyl, isobutoxymethyl); lower aliphatic acyloxy lower alkyl groups, (eg acetoxymethyl, propionyloxymethyl, butyryloxymethyl, pivaloyloxymethyl); lower alkoxycarbonyloxy lower alkyl groups (eg 1-methoxy-carbonyloxyethyl, 1-ethoxycarbonyloxyethyl); aryl lower alkyl groups (eg p-methoxybenzyl, o-nitrobenzyl, nitrobenzyl, benzhydryl and phthalidyl); tri(lower alkyl)silyl groups (eg trimethylsilyl and t-butyldimethylsilyl); tri(lower alkyl)silyl lower alkyl groups (eg trimethylsilylethyl); and (2–6C)alkenyl groups (eg allyl and vinylethyl).

Methods particularly appropriate for the removal of carboxyl protecting groups include for example acid-, base-, metal- or enzymically-catalysed hydrolysis.

Examples of hydroxyl protecting groups include lower alkoxycarbonyl groups (eg t-butoxycarbonyl); halo lower alkoxycarbonyl groups (eg 2-iodoethoxycarbonyl, 2,2,2-trichloroethoxycarbonyl); aryl lower alkoxycarbonyl groups (eg benzoloxycarbonyl, p-methoxybenzyloxycarbonyl, o-benzoyloxycarbonyl, nitrobenzyloxycarbonyl, p-nitrobenzyloxycarbonyl); tri lower alkylsilyl (eg trimethylsilyl, t-butyldimethylsilyl) and aryl lower alkyl (eg benzyl) groups.

A (1–4C)alkanoyl group (eg acetyl) may also be regarded as a hydroxyl protecting group in the context of the compounds of the invention in that compounds of formula I in which W and/or Z represent (1–4C)alkanoyloxy (eg acetoxy) groups (which are in themselves compounds of the invention) may readily be converted by conventional means into the corresponding hydroxy compounds.

Examples of amino protecting groups include formyl, aralkyl groups (eg benzyl and substituted benzyl, eg p-methoxybenzyl, nitrobenzyl and 2,4-dimethoxybenzyl, and triphenylmethyl); di-p-anisylmethyl and furylmethyl groups; acyl (eg alkoxycarbonyl and aralkoxycarbonyl eg t-butoxycarbonyl and benzyloxycarbonyl); trialkylsilyl (eg trimethylsilyl and t-butyldimethylsilyl); alkylidene (eg methylidene); benzylidene and substituted benzylidene groups; and the phthalimido group.

As noted above the cephalosporin derivatives of the invention have antibacterial properties. Thus they may be useful antibacterial agents, having a broad spectrum of activity in vitro against standard laboratory microorganisms, both Gram-negative and Gram-positive, which are used to screen for activity against pathogenic bacteria. The antibacterial spectrum and potency of a particular compound may be determined in a standard test system. The compounds have particularly high activity in vitro against strains of *Pseudomonas aeruginosa*.

The antibacterial properties of the compounds of the invention may also be demonstrated in vivo in conventional mouse protection tests.

Cephalosporin derivatives have generally been found to be relatively non-toxic to warm-blooded animals, and this generalisation holds true for the compounds of the present invention. A number of compounds were administered to mice at doses in excess of those required to afford protection against bacterial infections, and no overt toxic symptoms or side effects attributable to the administered compounds were noted.

According to a further feature of the invention there is provided a pharmaceutical composition which comprises a cephalosporin derivative of the invention in association with a pharmaceutically-acceptable diluent or carrier.

The pharmaceutical composition of the invention may, for example, be in a form suitable for oral, rectal or parenteral administration, for which purposes it may be formulated by means known to the art into the form of, for example, tablets, capsules, aqueous or oily solutions or suspensions, emulsions, dispersible powders, suppositories and sterile injectable aqueous or oily solutions or suspensions.

In addition to the cephalosporin derivative of the formula I the pharmaceutical composition of the invention may also contain, or be co-administered with, one or more known drugs selected from other clinically useful antibacterial agents (for example other beta-lactams or aminoglycosides), inhibitors of beta-lactamase (for example clavulanic acid), renal tubular blocking agents (e.g. probenicid) and inhibitors of metabolising enzymes (for example inhibitors of peptidases, for example Z-2-acylamino-3-substituted propenoates).

A preferred pharmaceutical composition of the invention is one suitable for intravenous, subcutaneous or intramuscular injection, for example a sterile injectable containing between 1 and 10% w/w of the cephalosporin derivative, or one suitable for oral administration in unit dosage form, for example a tablet or capsule which contains between 100 mg. and 1 g. of the cephalosporin derivative.

The pharmaceutical compositions of the invention will normally be administered to man in order to combat infections caused by bacteria, in the same general manner as that employed for cephalothin, cefoxitin, cephradine, ceftazidime and other known clinically used cephalosporin derivatives, due allowance being made in terms of dose levels for the potency of the cephalosporin derivative of the present invention relative to the known clinically used cephalosporins. Thus each patient will receive a daily intravenous, subcutaneous or intramuscular dose of 0.1 to 50 g., and preferably 0.5 to 10 g., of the cephalosporin derivative, the composition being administered 1 to 4 times per day. The intravenous, subcutaneous and intramuscular dose may be given by means of a bolus injection. Alternatively the intravenous dose may be given by continuous infusion over a period of time. Alternatively each patient will receive a daily oral dose which is approximately equivalent to the daily parenteral dose. Thus a preferred daily oral dose is 0.5 to 10 g. of the cephalosporin derivative, the composition being administered 1 to 4 times per day.

The invention is illustrated by, but not limited to, the following Examples in which the following abbreviations are used:

AcOH = acetic acid
DMF = dimethylformamide
DMSO = dimethylsulphoxide
EtOAc = ethyl acetate
EtOH = ethanol
HPLC = high performance liquid chromatography
MeOH = methanol
NMR = nuclear magnetic resonance spectroscopy
TEA = triethylamine
TFA = trifluoroacetic acid The NMR spectra are taken at 90 MHz and are quoted in terms of delta values in parts per million (ppm) with reference to tetramethylsilane (delta=0). The solvent used was $DMSOd_6/CD_3COOD/TFA$ except where otherwise indicated. In the quotation of NMR data s=singlet, d=doublet, t=triplet, q=quartet, m=multiplet, br=broad.

Reference may be made to our published European Patent Applications Nos. 127992 and 164944 for descriptions of methods suitable for the preparation of any cephalosporin starting materials used in the following Examples and not otherwise known in the chemical literature.

EXAMPLE 1

To a solution of 3-aminomethyl-7-[2-(2-aminothiazol-4-yl)-2-((Z)-1-carboxy-1-methylethoxyimino)acetamido]ceph-3-em-4-carboxylic acid (300 mg, 0.61 mmol) in dimethylformamide (3 ml) was added triethylamine (0.090 ml, 0.64 mmol) and 1-(3,4-diacetoxybenzoylmethyl)-4-methylthiopyrimidinium chloride (1.2 mmol). After 2 hours the mixture was evaporated to dryness under reduced pressure and purified by preparative HPLC on an octadecylsilane column using methanol/water (1% acetic acid) mixtures, followed by evaporation and freeze-drying to give 7-[(2-aminothiazol-4-yl)-2-((Z)-1-carboxy-1-methylethoxyimino) acetamido]-3-[N-(1-(3,4-diacetoxybenzoylmethyl)-4-pyrimidinio)aminomethyl]ceph-3-em-4-carboxylic acid (17%); 1.5(s,6H); 2.2(s,6H); 3.2–3.9(m,2H); 4.3 and 4.8(AB,2H); 5.1(d,1H); 5.8–6.2(m,3H); 6–7.2(m,6H); 8.7(m,1H).

EXAMPLE 2

In a manner similar to that of Example 1, 3-aminomethyl-7-[2-(2-aminothiazol-4-yl) 2-((Z) 1-carboxy-1-methylethoxyimino)acetamido]ceph-3-em-4-carboxylic acid was reacted with 1-(3,4-diacetoxybenzylmethyl) 4-methylthiopyrimidium chloride to give 7-[2-aminothiazol-4-yl)-2-((Z) 1-carboxy-1-methylethoxyimino)acetamido]-3-[N-1-(3,4-diacetoxybenzylmethyl) pyrimidinio)aminomethyl]ceph-3-em-4-carboxylic acid (58%); 1.5(s,6H); 2.2(s,6H); 3.3–3.7(m,2H); 4.2–4.8(m,2H); 5.1(d,1H); 5.3(s,2H); 5.8(d,1H); 6.8–7.4(m,5H); 8.2(m,1H); 8.9(s,1H).

EXAMPLE 3

In a manner similar to Example 1, 3-aminomethyl-7-[2-(2-aminothiazol-4-yl)-)-2-((Z)-1-carboxy-1-methylethoxyimino)acetamido]ceph-3-em-4-carboxylic acid was reacted with 1-(3,4-diacetoxybenzylmethyl)-4-methylsulphinylpyridinium chloride to give 7-[(2-aminothiazol-4-yl)-2-((z)-1-carboxy-1-methylethoxyimino)acetamido]-3-[N-(1-(3,4-diacetoxybenzylmethyl)-4-pyridinio)aminomethyl]ceph-3-em-4-carboxylic acid (13%); 1.5(s,6H); 2.2(s,6H); 3.5(m,2H); 4.3(br,2H); 5.2(d,1H); 5.3(s,2H); 5.8(d,1H); 6.8–7.6(m,6H); 8.1–8.6(m,2H).

EXAMPLE 4

In a manner similar to Example 1, 3-aminomethyl-7-[2-(2-aminothiazol-4-yl)-2-((Z)-1-carboxy-1-methylethoxyimino)acetamido]ceph-3-em-4-carboxylic acid was reacted with 1-(3,4-diacetoxybenzoylmethyl)-thieno[2,3 d]-4-methylthiopyrimidinium chloride to give the corresponding di-acetoxy cephalosporin. Prior to isolation the reaction mixture was evaporated to dryness under reduced pressure and was redissolved in aqueous sodium bicarbonate (pH9). After one hour the pH was adjusted to 2 and the resultant mixture was purified by HPLC to give 7-[(2-aminothiazol-4-yl)-2-((Z)-1-carboxy-1-methylethoxyimino)acetamido]-3-[N-(1-(3,4-dihydroxybenzoylmethyl)thieno[2,3-d]-4-pyrimidinio)aminomethyl]ceph-3-em -4-carboxylic acid (16%) 1.5(s,6H); 3.6–3.9(m,2H); 4.4–5.3(m,3H); 5.9(d,1H); 6.1(s,2H); 6.8–7.1(m,2H); 7.4–7.7(m,2H); 7.8–9.1(m,2H); 8.8(s,1H).

EXAMPLE 5

In a manner similar to Example 1, 3-ethylaminomethyl- 7-[2-(2-aminothiazol-4-yl)-2-((Z)-1-carboxy-1-methylethoxyimino)acetamido]ceph-3-em-4-carboxylic acid (317 mg, 0.61mmol) was reacted with 1-(3,4-diacetoxybenzylmethyl)-4-methylthiopyrimidinium chloride to give 7-[(2-aminothiazol-4-yl) 2((Z)-1-carboxy-1-methylethoxyimino)acetamido]-3-[N-ethyl-N-(1-(3,4-diacetoxybenzylmethyl) 4-pyrimidinio)aminomethyl]ceph-3-em-4-carboxylic acid (6%); 1.1(m,3H); 1.5(s,6H); 2.2(s,6H); 3.2–4(m,4H); 4.2–5.6(m,5H); 5.8(d,1H); 7–7.5(m,5H); 8.4(d,1H); 9.0(s,1H).

EXAMPLE 6

In a manner similar to Example 5, 3-ethylaminomethyl-7-[2-(2-aminothiazol-4-yl)-2-((Z)-1-carboxy-1-methylethoxyimino)acetamido]ceph-3-em-4-carboxylic acid was reacted with 1-(3,4-diacetoxybenzylmethyl)-thieno[2,3-d]4-methylthiopyrimidinies chloride to give 7-[(2-aminothiazol-4-yl)-2-((Z)-1-carboxy-1-methylethoxyimino)acetamido]-3-[N ethyl-N-(1-(3,4-diacetoxybenzylmethyl)thieno[2,3-d]-4-pyrimidinio)aminomethyl]ceph-3-em-4-carboxylic acid (22%); 1–2.7(m,9H); 2.2(s,6H); 3.5(br,2H); 4(br,2H); 4.5–5.5(m,3H); 5.5–6(m,6H); 7(s,1H); 7.1–8(m,5H); 9.1(s,1H).

EXAMPLE 7

To a solution of 3-ethylaminomethyl-7-[2 (2-aminothiazol-4-yl)- 2-((Z)-1-carboxy-1-methylethoxyimino)acetamido]ceph-3-em-4-carboxylic acid (325 mg, 0.68 mmol) and sodium bicarbonate (160 mg. 1.9 mmol) in a mixture of dimethylformamide (3 ml) and water (3 ml) was added 1-(3,4 diacetoxybenzylmethyl)-thieno[2,3 d]4-chloropyridinium chloride (1.2 mmol). After heating at 40° C. for 2 hours the mixture was evaporated to dryness under reduced pressure and purified by preparative HPLC on an octadecylsilane column using methanol/water (1% acetic acid) mixtures to give 7-[(2-aminonothiazol-4-yl)-2((Z)-1-carboxy-1- methylethoxyimino)acetamido]-3-[N-ethyl-N-(1-(3,4-diacetoxybenzylmethyl)thieno[2,3-d]-4-pyridinio)aminomethyl]ceph-3-em-carboxylic acid (12%); 1.1–1.6(m,9H); 2.2(s,6H); 3.3–4(m,4H); 4.9(br,2H); 5.1 (d,1H); 7–7.4(m,5H); 7.6–7.8(br,2H); 8.6(d,1H)

EXAMPLE 8

In a manner similar to Example 1, 3 aminomethyl-7-[2-(2-aminothiazol-4-yl) 2-((Z)-methoxyimino)acetamido]ceph-3-em-4-carboxylic acid was reacted with 1-(3,4-diacetoxybenzoylmethyl)-4-methylthiopyrimidinium chloride to give 7-[(2-aminothiazol-4-yl) 2((Z)-methoxyimino)acetamido]-3-[N-(1-(3,4-diacetoxybenzoylmethyl)-4-pyrimidinio)aminomethyl]-ceph-3-em-4-carboxylic acid (20%); 2.3(s,6H); 3.6(m,2H); 3.9(s,3H); 4.3(d,1H); 4.9(d,1H); 5.2(d,1H); 5.7–6(m,3H); 7–8.2(m,6H); 8.7(s,1H).

EXAMPLE 9

In a manner similar to Example 1, 3-aminomethyl-7-[2-(2-aminothiazol-4-yl)-2-((Z)-ethoxyimino)acetamido]ceph-3-em-4-carboxylic acid was reacted with 1-(3,4-diacetoxybenzylmethyl) 4-methylthiopyrimidinium chloride to give 7-[2-(2-aminothiazol-4-yl)-2-((Z)ethoxyimino)acetamido]-3-[N-(1-(3,4-diacetoxybenzylmethyl)-4-pyrimidinio)aminomethyl]-ceph 3-em-4-carboxylic acid (26%); 1.2(t,3H); 2.2(s,6H); 3.3–3.8(AB,2H); 4.1–4.8(m,4H); 5.1(d,1H); 5.3(s,2H); 5.8(d,1H); 6.9–7.5(m,5H); 8.2 8.3(m,1H); 9(s,1H).

EXAMPLE 10

In a manner similar to Example 1, 3-ethylaminomethyl-7-[2-(2-aminothiazol-4-yl)-2-((Z)-ethoxyimino)acetamido]-ceph-3-em-4-carboxylic acid was reacted with 1-(3,4-diacetoxybenzylmethyl) 4-methylthiopyrimidinium chloride to give 7-[2-(2-aminothiazol-4-yl)-2-((Z) ethoxyimino)acetamido]-3-[-ethyl-(1-(3,4-diacetoxybenzylmethyl)-4-pyrimidinio)-aminomethyl]-ceph-3-em-4-carboxylic acid (40%); 1–1.4(m,6H); 2.2(s,6H); 3.2–4(m,4H); 4.4–5.2(m,2H); 5.3(s,2H); 5.8(d,1H): 6.9–7.4(m,5H); 8.2–5(m,1H); 8.9–9.1(m,1H).

EXAMPLE 11

In a manner similar to Example 1, 3-aminomethyl-7-[2-(2-aminothiazol-4-yl)-2-((Z)-ethoxyimino)acetamido]ceph-3-em-4-carboxylic acid was reacted with 1-(3,4-diacetoxybenzylmethyl)-4-methylsulphinylpyridinium chloride to give 7-[2-(2(2-aminosinothiazol-4-yl)-2-((Z)-ethoxyimino)acetamido]-3-[N-(1-(3,4-diacetoxybenzylmethyl)-4-pyridinio)aminomethylrceph-ceph-3-em-4-carboxylic acid (58%); 1.3(t,3H); 2.2(s,6H); 3.4–3.6(AB,2H); 4–4.5(m,4H); 5.1(d,1H): 5.3(s,2H); 5.8(d,1H); 7(m,3H): 7.3(s,3H); 8 8.6(m,2H).

EXAMPLE 12

The reaction of Example 10 was repeated using the 3'-N-ethyl analogue having a 2-chloroethoxyimino grouping to give 7-[2-(2-aminothiazol-4-yl)-2-((Z)-2-chloroethoxyimino)acetamido]-3-[N-ethyl-N-(1-(3,4-diacetoxybenzylmethyl)-4-pyrimidinio)aminomethyl]-ceph-3-em-4-carboxylic acid (5%); 1.2(s,3H); 2.2(s,6H); 3.4–4(m,4H); 4–5.6(m,9H); 5.8(d,1H); 6.8–7.6(m,5H); 8.3(d,1H); 9.1(s,1H).

EXAMPLE 13

The 3-ethylaminomethyl cephalosporin starting material of Example 12 was contaminated with the corresponding 3-aminomethyl cephalosporin. On purification 7-[2-(2-aminothiazol-4-yl)-2-((Z)-2-chloroethoxyimino)acetamido]-3-[N-(1-(3,4-diacetoxybenzylmethyl)-4-pyrimidinio)aminomethyl]ceph-3-em-4-carboxylic acid was obtained (5%); 2.2(s,6H); 3.4–4(m,2H); 4 5.6(m,9H); 5.8(d,1H); 6.8 7.6(m,5H); 8.3(d,1H); 9.1(s,1H).

EXAMPLE 14

The product of Example 11 (0.23 g, 0.32 mmol) in water (1 ml) and methanol (1ml) was adjusted to pH8.5 with aqueous sodium bicarbonate. After two hours the mixture was acidified to pH2, purified on a HP20SS resin column, evaporated and freeze-dried to give 7-[2-(2-aminothiazol-4-yl) 2-((Z)-ethoxyimino)acetamido]-3-[N-(1-(3,4-dihydroxybenzylmethyl) 4-pyridinio)aminomethyl]ceph-3-em-4-carboxylic acid (65%); 1.2(s,3H); 3.3–3.6(AB,2H); 3.9–4.6(m,4H); 5.1(m,3H); 5.7(d,1H), 6.4–7.4(m,6H); 7.9–8.6(m,2H).

EXAMPLE 15

7-[2-(2-Aminothiazol-4-yl)-2-((Z)-1-carboxy-1-methylethoxyimino) acetamido]3-[N-ethyl-N-[1-(2-(3,4-dihydroxybenzoylamino)ethyl)-4-pyridinio]aminomethyl]-ceph-3-em-4-carboxylate To a solution of 7-[2-(2-aminothiazol-4-yl)-2-((Z)-1-carboxy 1-methylethoxyimino)acetamido]-3-[N-ethyl-N-(1-(2-aminoethyl)-4-pyridinio)-aminomethyl]ceph-3-em-4-carboxylate (0.145 mmole)in MeOH (10 ml) at 0° C. was added TEA (0.435 mmole) and solid 3,4-diacetoxybenzoyl chloride (0.145 mmole). After 2 h the mixture was acidified with AcOH and evaporated to dryness under reduced pressure to give the di-acetoxy compound.

To remove the acetoxy groups the residue was dissolved in an aqueous solution of sodium bicarbonate, adjusted to pH 8.5 and maintained at this pH for 2 h. The mixture was then acidified to pH 2.0 with HCl (2N), evaporated to dryness and the residue purified on a column of 'Diaion' HP 20 SS resin using MeOH/water mixtures of increasing proportions of MeOH and containing AcOH (1%). Evaporation and freeze drying gave the title compound, (31%). NMR 1.1(t,3H); 1.5(s,6H): 3.1–3.9(m,6H); 4.1–4.5(m,2H); 4.6(m,2H); 5.2(d,1H); 5.9(d,1H); 6.8(d,1H); 7.0(s,1H); 6.9–7.3(m,4H); 8.2(d,2H).

EXAMPLE 16

7-[2-(2-Aminothiazol-4-yl)-2-((Z)-1-carboxy-1-methylethoxyimino) acetamido]-3-[N-ethyl-B-[-1-(2-(3,4-dihydroxybenzoylamino) ethyl)thieno[2,3-d]-4-pyridinio]aminomethyl]ceph-3-em-4-carboxylate The process of Example 15 was repeated, using the appropriate cephalosporin starting material to yield 19% of the title compound, NMR 1.3(t,3H); 1.5(s,6H); 3.3–4.0(m,6H): 4.4 4.7(m,2H); 4.8(m,2H); 5.2(d,1H): 5.9(d,1H); 6.7(d,1H); 7.0(s,1H) 6.9 7.3(m,3H); 7.6–7.9(m,2H); 8.1–8.5(m,1H).

EXAMPLE 17

To a stirred soltion of 3-aminomethyl-7-[2-(2-aminothiazol-4-yl) 2-((Z)-1-carboxy-1-methylethoxyimino)acetamido]ceph-3-em-4-carboxylic acid (400 mg, 0.82 mmol) and sodium bicarbonate (208 mg, 2.5 mmol) in a mixture of dimethylformamide (3 ml) and water (3 ml) was added the appropriate heterocyclic starting material:

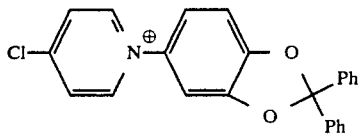

(458 mg, 1.3 mmol). The pH was adjusted and maintained at 7.5 for 2 hours. The mixture was then evaporated to dryness under reduced pressure to give the hydroxy protected cephalosporin. This was redissolved in a solution of trifluoroacetic acid water (90:10) (5 ml), stirred for one hour and evaporated to dryness. The residue was purified by preparative HPLC on an octadecylsilane solumn using methanol/water (1% acetic acid) mixtures to give 7-[2-(2-aminothiazol-4yl)-2-((Z)-1-carboxy-1-methylethoxyimino)acetamido]-3-[N-(1-(3,4-dihydroxyphenyl)-4-pyridinio)aminomethyl]ceph-3-em-4-carboxylic acid (5%): 1.55(s,6H); 3.3–3.7(m,2H); 4.4(br,2H); 5.15(d,1H); 5.75(d,1H); 6.7–8.2(m,6H); 8.1–8.5(m,2H).

EXAMPLES 18-20

In a manner similar to that of Example 17, the heterocyclic starting material depicted therein was reacted with 3-ethylaminomethyl 7-[2-(2-aminothiazol-4-yl)-2-((Z)-1-carboxy-1-methylethoxyimino)acetsido]ceph-3-em-4-carboxylic acid, 3-aminomethyl-7-[2-(2-aminothiazol-4-yl)-2-((Z)-ethoxyimino)acetamido]ceph-3-em-4-carboxylic acid, and 3-ethylaminomethyl 7-[2-(2-aminothiazol-4-yl)-2-((Z)-ethoxyimino)acetamido]-ceph-3-em-carboxylic acid respectively to give the corresponding protected hydroxy cephalosporin derivatives. These were hydrolysed and purified, as in Example 17, to give respectively:

7-[2-(2-aminothiazol-4-yl)-2-((Z)-1-carboxy-1-methylethoxyimino)acetamino]--
-3-[N-ethyl-N-(1-(3,4-dihydroxyphenyl)-4-pyridinio)aminomethyl]ceph-3-em-4-carboxylic acid (11%); 1.7(s,3H); 1.55(s,6H); 3–4(m,4H); 4.7(br,2H); 5.2(d,1H); 5.9(d,1H); 6.8–7.5(m,6H); 8.4(d,2H), 7-[2-(2-aminothiazol-4-yl)-2-((Z)-ethoxyimino)acetamido]3-[N-(1-(3,4-dihydroxyphenyl) -4-pyridinio)aminomethyl]ceph-3-em-4-carboxylic acid (25%); 1.3(t,3H); 3.55(m,2H); 4–4.6(m,4H); 5.15(d,1H); 5.8(d,1H); 6.8–7.2(m,6H); 6.95(m,2H), and 7-[2-(2-aminothiazol-4-yl)-2-((Z)-ethoxyimino)acetamido]-3-[N-ethyl-N-(1-(3,4-dihydroxyphenyl)-4-pyridinio)aminomethyl]ceph 3-em-4-carboxylic acid (10%); 1.35(m,6H); 3 4(m,4H); 4–4.6(m,2H); 4.7(br,2H); 5.1(d,1H); 5.9(d,1H); 6.8 7.6(m,6H); 8.3–8.7(m,2H).

EXAMPLE 21

In a manner similar to that of Example 17, 3-aminomethyl-7-[2-(2-aminothiazol-4-yl)-2-((Z)-ethoxyimino)acetamido]ceph-3-em-4-carboxylic acid was reacted with:

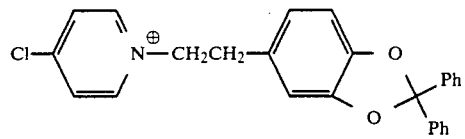

to give the hydroxy protected cephalosporin. This was hydrolysed and purified to give 7-[2-(2-aminothiazol-4-yl)-2-((Z)-ethoxyimino)acetamido]-3-[N-(1-(2-(3,4-dihydroxyphenyl)ethyl)-4-pyridinio)aminomethyl]-ceph-3-em-4-carboxylic acid (12%); 1.2(t,3H); 2.9(3.2H); 3.35 and 3.6(AB,2H); 4–4.4(m,6H): 5.15(d,1H); 5.8(d,1H); 6.2–7(m,6H); 8(br,2H).

EXAMPLE 22

In a manner of Example 16, the same cephalosporin starting-material (as in Example 16) was reacted with 3-bromo-4,5-di-acetoxybenzoyl chloride to give the di-acetoxy compound which was subsequently purified on Diaion HP20SS resin prior to deprotecting at pH8.5 to give 7-[2-(2-aminothiazol-4-yl)-2-((Z)-1-carboxy-1-methylethyoxyimino)acetamido]-3-[N-ethyl)-[1-(2-(3-bromo-4,5-dihydroxybenzoylamino)-ethyl)thieno[2,3 d]-4-pyridinio]aminomethyl]ceph-3-em-4-carboxylic acid; 1.3(t,3H); 1.5(s,6H); 3.2–4.0(m,6H); 4.3–50(m,4H); 5.15(d,1H); 5.9(d,1H); 7.0(s,1H); 7.0–7.4(m,3H); 7.8(m,2H); 8.3(m,1H).

EXAMPLE 23

To a solution of 4-chloro-2-(3′,4′-diacetoxyphenyl) 1-methyl pyridinium tetrafluoroborate (2.6mmole) in $CH_2Cl_2$ (2 ml) was added a mixture of 3-aminomethyl-7-[2-(2-aminothiazol-4-yl)-2-[(Z)-1-carboxy-1-methylethoxyimino)acetamido]ceph-3-ethoxy-carboxylic acid (1.26 g, 2.6mmole), triethylamine (1.08 ml; 6.7 mmole) and DMF (10 ml). The reaction mixture was stirred for 2 hr at room temperature and stored in the refrigerator overnight. The following morning the dichloromethane was removed under reduced pressure, the resulting DMF solution diluted with water (5 ml) and the pH adjusted to 5 with acetic acid. The solution was filtered and the filtrate purified by chromatography on a DYNAMAX column ($C_{18}$ reverse phase silica, 21.5 mm×250 mm). The eluent was 25% $CH_3CN$, 75% $H_2O$, 0.1% TFA. The fractions which by HPLC (Hichrom, ODS-2, reverse phase silica) were shown to contain the desired product were combined, the $CH_3CN$ removed under reduced pressure and the aqueous solution so obtained freeze dried to give 7- [2-(2-aminothiazol-4-yl)-2-((Z)-1-carboxy-1-methylethoxyimino)acetamido]-3-N-[2-(3′,4′-diacetoxyphenyl)-1-methyl)pyridinio]aminomethyl]-3-cephem-4-carboxylic acid ($D_6DMSO,d_4HOAc$): 1.45(s,3H); 1.43(s,3H); 2.28(s,3H); 2.30(s,3H); 3.45(d,1H); 3.65(d,1H); 3.68(s,3H); 4.2–4.40(m,2H); 5.15(d,1H); 5.86(d,1H); 6.73(s,1H); 6.85–7.70(m,5H); 8.25, 8.47(d,d,1H).

The above diacetoxy derivative (150 mg) was stirred, at room temperature for 2 hrs, with a solution of ammonium carbonate (150 mg) in water (6 ml). The reaction mixture was acidified with 2NCH1 and DMSO (3 ml) added to maintain a clear solution. The solution was applied to a DYNAHAX column (21.5 mm×250 mm) and the desired product eluted with 20% $CH_3CN$, 80% $H_2O$, 0.1% TFA. The appropriate fractions were combined, the CH₃CN evaporated under reduced pressure, and the aqueous solution freeze dried to give: 7-[2-(2-aminothiazol-4-yl)-2-((Z)-1-carboxy-1-methylethoxyimino)acetamido]-3-N-[2-(3,4-dihydroxyphenyl)-1-methyl)-4-pyridinio]aminomethyl]-3-cephem-4-carboxyic acid (73 mg). NMR d₆DMSO, d₄HOAC: 1.43(s,3H); 1.45(s,3H); 3.42(d,1H); 3.63(d,1H); 3.65(s,3H); 4.25(d,1H); 4.40(d,1H); 5.17(d,1H); 5.83(d,1H); 6.78(s,1H); 6.7–7.1(m,5H); 8.10–8.30(d,d,1H). FAB M.S. 684(m+H)+.

EXAMPLE 24

A solution of 4-chloro-2-(3',4'-diacetoxyphenyl)-1-methyl pyridinium tetrafluoroborate (0.1 mmole) in CH₂Cl₂ (1 ml) was added to a solution of 3-ethylaminomethyl-7-[2-aminothiazol-4-yl)-2-((Z)-1-carobxy-1-methylethoxyimino)acetamido]ceph-3-em-4-carboxylate (51.2 mg, 0.1 mmole) in DMF (1 ml) containing triethylamine (0.05 ml, 0.35 m mmole). The reaction mixture was stirred overnight at room temperature before being evaporated to dryness under reduced pressure. The gum so obtained was then treated with (NH₄)₂CO₃ (50 mg) in H₂O (1 ml). The precipitate which was initially formed dissolved during stirring overnight. The solution was applied to a DYNAMAX column and the product eluted with 22% CH₃CN, 78% H₂O, 0.1% TFA. The appropriate fractions were combined, the CH₃CN removed under reduced pressure and the aqueous solution freeze-dried to give 7-[2-(2-aminothiazol-4-yl)-2-((Z)1-carboxy-1-methylethoxyimino)-acetamido]-3-[N-ethyl-N-[2-(3,4-dihydroxyphenyl)-1-methyl)-4-pyridinio]aminomethyl -3-cephem-4-carboxylic acid. NMR d₆DMSO, d₄HOAc: 1.10(m,3H); 1.45(s,3H); 1.47(s,3H); 3.24(d,1H); 3.52(d,1H); 3.6(m,2H); 3.68(s,3H); 4.55(d,1H); 4.68(d,1H); 5.17(d,1H); 5.83(d,1H); 6.75(s,1H); 6.73–7.25(m,5H); 8.26(d,1H). M.S. (+ve FAB) 712 M+H)+.

EXAMPLE 25

In a manner of Example 23, the pyridinium compound and 3-aminomethyl-7-[2-aminothiazol-4-yl)-2-((Z)-ethoxyimino)acetamido]ceph-3-em-4-carboxylic acid were reacted to give 7-[2-(2-aminothiazol-4-yl)2-((Z)ethoxyimino)acetamido]-3-N [2-(3',4'-dihydroxyphenyl)-1-methyl)pyridinio]aminomethyl]-3-cephem-4-carboxylic acid NMR (d₆DMSO, d₄HOAc): 1.22(t,3H); 3.40(d,1H); 3.60(d,1H); 3.65(s,3H); 4.08(q,2H); 4.25(d,1H); 4.40(d,1H); 5.15(d,1H); 5.78(d,1H); 6.75(s,1H); 6.8–7.1(m,5H); 8.1–8.35(d,d,1H); m.s. (+ve FAB) 626 (M+H)+

EXAMPLE 26

To a solution of 3-aminomethyl-7-[2-(2-aminothiazol-4-yl)-2-((Z)-1-carboxy-1-methylethoxyimino)acetamido]ceph-3-em-4-carboxylic acid (320 mg, 0.75 mmol) in dimethylformamide (4 ml) was added triethylamine (108 μl, 0.75 mmol) and 1-methyl-4-methylthio-6,7-diisobutyroxyquinazolinium tetrafluoroborate (0.85 mmol). After 30 minutes the reaction mixture was evaporated under reduced pressure; the residue of protected quinazolinium cephem was redissolved in methanol/water (50:50) (5 ml) and the pH maintained at 8.2 for 30 minutes. The mixture was evaporated to dryness and purified on a Diaion HP20SS resin column using methanol/water (1% acetic acid) to give 7-[(2-aminothiazol-4-yl)-2-((Z)-1-carboxy-1-methylethoxyimino) acetamido]-3-[(6,7-dihydroxy-1-methyl-4-quinazolinio)aminomethyl]ceph-3-em-4-carboxylic acid (25%); 1.5(s,6H); 3.55(br,2H); 3.9(s,3H); 4.4–5.2(m,3H), 5.85(d,1H), 7.0(s,1H); 7.2(s,1H); 7.7(s,1H); 8.7(s,1H).

EXAMPLE 27

In a manner similar to Example 26, 3-aminomethyl-7-[2-(2-aminothiazol-4-yl)-2-((Z)-1-ethoxyimino)acetamido]ceph-3-em-4-carboxylic acid was reacted with 1-methyl-4-methylthio-6,7-di-n-butyroxy quinazolinium tetrafluoroborate to give the protected quinazolinium cephem and subsequently 7-[(2-aminothiazol-4-yl)-2-((Z)-ethoxyimino)acetamido]-3-[(6,7-dihydroxy-1-methyl-4-quinazolinio)aminomethyl]ceph-3-em-4-carboxylic acid (12%); 1.3(m,3H); 3.55(br,2H); 3.9(s,3H); 4–4.9(m,4H); 5.1(d,1H); 5.8(d,1H); 7.0(br,1H); 7.2(s,1H); 7.75(s,1H); 8.7(s,1H).

EXAMPLE 28

To a stirred solution of 3-aminomethyl-7-[2-(2-aminothiazol-4-yl)-2-(Z)-carboxy-1-methylethoxyimino)acetamido]ceph-3-em-4-carboxylic acid (530 mg, 1.09 mmol) in a mixture of dimethylformamide (5 ml) and water (5 ml) was added 1-ethyl-4-chloro-6,7-dipivaloyloxyquinolinium chloride (1.2 mmol). The pH of the solution was adjusted and maintained at 7.5 for 2 hours by the addition of sodium bicarbonate. The mixture was evaporated and the residue purified by preparative HPLC on an octadecylsilane column using methanol/water (1% acetic acid) to give 7-[(2-aminothiazol-4-yl)-2-((Z)-1-carboxy-1-methylethoxyimino)acetamido]-3-[1-ethyl-6,7-dipivaloyloxy-4-quinolinio]aminomethyl]ceph-3-em-4-carboxylic acid (5%), 1–1.8(m,27H), 3.6(br,2H); 4.6(br,4H); 5.2(d,1H); 5.85(d,1H); 7(br,2H); 8.1(s,1H); 8.5(s,1H); 8.75(d,1H).

EXAMPLE 29

To a suspension of 3-aminomethyl-7-[2-(2-aminothiazol-4-yl)-2-((Z)-ethoxyimino)acetamido]ceph-3-em-4-carboxylic acid (250 mg, 0.59 mmole) and 1-methyl-6-(3,4-diacetoxyphenyl)-4-methylthiothieno[2,3-d]pyrimidinium tetrafluoroborate (117 mg, 0.25 mmole as a 5:1 mixture with its 2-methyl isomer) in methanol and under argon, triethylamine (70 μl) was added with vigorous stirring. After 2 hours a further portion of triethylamine (35 μl) was added (0.75 mmole in total) and the reaction allowed to stir overnight. Diethyl ether was added to precipitate the reaction products, which were filtered and washed with ether to give a brick-red solid (262 mg). This was transferred to the top of a 2 cm HP20SS resin column in a 50:50 water/DMF mixture and eluted with increasing concentrations of acetonitrile in water. The desired product, deprotection of the di-acetoxy derivative having occured on the column, was observed to elute with 40% CH₃CN/H₂O. Acetonitrile was removed on a cold-finger Buchi and the product freeze-dried to give 7-[(2-aminothiazol-4-yl)-2-((Z)-ethoxyimino)acetamido]-3-[N-(6-(3,4-dihydroxyphenyl)-1-methylthieno[2,3-d]-4-pyrimidinio)-aminomethyl]ceph-3-em-4-carboxylate (61 mg) NMR (d₆DMSO, d₄HOAc): 1.91(3H,t), 3.48(1H,d), 3.63(1H,d); 4.02(3H,s), 4.08(2H,q); 4.56(1H,d); 4.92(1H,d); 5.08(1H,d); 5.78(1H,d); 6.70(1H,s); 6.87(1H,d); 7.01(1H,dd); 7.10(1H,d); 8.01(1H,s); 8.79(1H,s); FAB m/s 683 (M+H)+.

EXAMPLE 30

To a stirred suspension of 3-aminomethyl-7-[2-(2-aminothiazol-4-yl)-2-((Z)-1-carboxy-1-methylethoxyimino)acetamido]ceph-3-em-4-carboxylic acid (210 mg, 0.43 mmole) and 1-methyl-6-(3',4'-diacetoxyphenyl)-4-methylthiothieno[2,3-d]pyrimidinium tetrafluoroborate (145 mg, 0.3 mmole) in methanol (4 ml) under argon, triethylamine (146 μl, 1.05 mmole) was added dropwise. After 7 hours, a further 20 μl of triethylamine was added. The reaction products were precipitated by addition of ether and 4 drops of acetic acid, and filtered to give crude diacetoxy compound as a brick-red solid (221 mg). This was taken up in DMF (20 ml) and a solution of ammonium carbonate (200 mg) in water (50 ml) added to adjust pH between 8.0–9.0. After 1 hour, the pH was readjusted to pH4 with acetic acid, and extra DMF added to effect solution. Elution on a HP20SS resin column (2 cm diameter) with increasing proportions of acetonitrile in water gave 208 mg of a yellow powder after evaporation and freeze drying, which was identified as 7-[2-(2-aminothiazol-4-yl)-2-((Z)-1-carboxy-1-methylethoxyimino)acetamido]-3-[N-(6-(3,4-dihydroxyphenyl)-1-methylthieno[2,3-d]-4-pyrimidinio)aminomethyl]ceph-3-em-4-carboxylic acid; NMR (d6DMSO, d4HOAc); 1.42(3H,s); 1.44(3H,s); 3.47(1H,d); 3.65(1H,d); 4.02(3H,s); 4.56(1H,d); 4.91(1H,d); 5.10(1H,d); 5.83(1H,d); 6.73(1H,s); 6.88(1H,d); 7.02(1H,dd); 7.09(1H,d); 8.00(1H,s); 8.78(1H,s); FAB m/s 739 (M-H)+.

EXAMPLE 31

The procedure used for Example 30 was repeated using 1-methyl-6-(3,4-isobutyroxybenzoyl-4-methylthiothieno[2,3-d]-pyrimidinium tetrafluoroborate. The product 7-[2-(2-aminothiazol-4-yl)-2-((Z)-1-carboxy-1-methylethoxyimino)-acetamido]-3-[N-(6-(3,4-dihydroxybenzoyl)-1-methyl-thieno[2,3-d]-4-pyrimidinio)aminomethyl]ceph-3-em-4-carboxylic acid was characterised by NMR (d6DMSO,d4HOAc): 1.42(3H,s); 1.44(3H,s); 3.44(1H,d); 3.63(1H,d); 4.05(3H,s); 4.58(1H,d); 4.91(1H,d); 5.10(1H,d); 5.83(1H,d); 6.72(1H,s); 6.97(1H,d); 7.38(1H,d); 7.39(1H,dd); 8.63(1H,s); 8.91(1H,s).

EXAMPLE 32

To a stirred solution of 3-aminomethyl-7-[2-(2-aminothiazol-4-yl)-2-((Z)-1-carboxycyclobutoxyimino)acetamido]ceph-3-em-4-carboxylic acid (0.5 mmol) and sodium bicarbonate (2.5 mmol) in water (5 ml) was added a solution of 1-(5-methoxypyran-4-on-2-yl)-4-methylsulphinylpyridinium chloride (1.0 mmol) in water (2 ml). The mixture was stirred at room temperature for 18 hours, acidified with acetic acid and sufficient sodium acetate was added to redissolve any precipitated product. The mixture was subjected to column chromatography on Sepabead using aqueous acetonitrile in a gradient elution, to give, after evaporation and freeze-drying, 7-[2-(2-aminothiazol-4-yl)-2-((Z)-1-carboxy cyclobutoxyimino)acetamido]-3-[N-(1-(5-methoxypyran-4-on-2-ylmethyl)-4-pyridinio)aminomethyl]ceph-3-em-4-carboxylic acid (55%), NMR (DMSO-d6/CD3CO2D): 1.85(6H); 2.4(4H); 3.27(s,2H); 3.50(q,2H); 3.61(s,3H); 4.32(q,2H); 5.14(d,1H); 5.81(d,1H); 6.40(s,1H); 6.75(s,1H); 7.04(octet,2h); 7.99(s,1H); 8.21(q,2H).

EXAMPLES 33–36

In a manner similar to Example 32 in the following cephalosporins were obtained from the corresponding 3-aminomethylceph-3-em and the appropriate heterocycle.

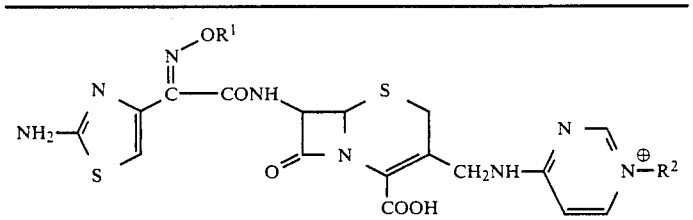

-continued

| Example | R¹ | R² |
|---|---|---|
| 36 | CH₃-C(CH₃)-COOH | pyridine with OH, OH, -CH₂CO- |

Footnotes to Table

Example 33; reaction performed using 2 equivalents of heterocycle and 5 equivalents of triethylamine in methanol. Product isolated as triethylamine salt after trituration with methanol.

Example 34; reaction performed using 1½ equivalents of heterocycle and 5 equivalents of triethylamine. The product was purified by chromatography on HP20SS under medium pressure to give the triethylamine salt after trituration with acetone.

Example 35; reaction performed using 1½ equivalents of heterocycle and 4 equivalents of triethylamine. The product was purified on HP20SS (medium pressure) to give the zwitterion.

Example 36; reaction performed substantially as for Example 34.

NMR Data for the Products of Examples 33–36 (DMSO-d₆/CD₃CO₂D)

Example 33: 1.17(t,9H); 1.85(m); 2.38(m); 3.08(q,6H); 3.52(q,2H); 4.48(q,2H); 5.10(d,1H); 5.28(s,2H); 5.83(d,1H); 6.55(s,1H); 6.76(s,1H); 6.95(d,1H); 8.00(s,1H); 8.19(q,1H); 8.90(s,1H).

Example 34: 1.16(t,9H); 1.45(d,6H); 3.08(q,6H); 3.50(q,2H); 4.47(q,2H); 5.10(d,1H); 5.22(s,2H); 5.80(d,1H); 6.74(s,1H); 6.76(s,1H); 6.91(d,1H); 7.88(s,1H); 8.15(q,1H); 8.89(s,1H).

Example 35: 1.21(t,3H); 3.53(q,2H); 4.09(q,2H); 4.48(q,2H); 5.19(d,1H); 5.25(s,2H); 5.79(d,1H); 6.72(s,1H); 6.77(s,1H); 6.90(d,1H); 7.80(s,1H); 8.18(q,1H); 8.89(d,1H).

Example 36: 1.17(t,9H); 1.44(d,6H); 3.08(q,6H); 3.56(q,2H); 4.28(s); 4.51(q,2H); 5.14(d,1H); 5.85(d,1H); 6.74(s,1H); 6.96(d,1H); 7.46(s,1H); 8.12(q,1H); 8.14(s,1H); 8.75(d,1H).

Preparation of Starting Materials

The heterocyclic starting material for Examples 1 and 8 (1-(3,4-diacetoxybenzoylmethyl)-4-methylthiopyrimidinium chloride) was prepared by heating 4-methylthiopyrimidine (252 mg, 2 mmoles) and 2-chloro-3',4'-diacetoxyacetophenone (541 mg, 2 mmoles) at 80° C. for 1 hour in the presence of DMF (0.25 ml). After cooling the mixture was triturated with ethyl acetate and the resulting solid was filtered off.

The above general process was used to prepare the starting materials for the compounds of Examples 2,4–6,9, 10, 12 and 13.

The starting material for Example 7 was prepared using the corresponding chloro derivative in place of the methylthio compound.

The starting material for Examples 3, 11 and 14 was prepared as follows.

4-methylthio-1-(3,4-diacetoxybenzyl)pyridinium chloride was prepared by the method given above and then 1.5 g (3.6 mmoles) was further oxidised using meta-chloroperoxybenzoic acid (1.5 g, 7.2 mmole) in dichloromethane/TFA. After 2 hours the solvents were evaporated and the residue triturated with ether. The resulting solid was filtered off and used without further purification.

TABLE 1

| Starting material for Example No(s) | Formula | NMR |
|---|---|---|
| 1,8 | CH₃S-pyridinium-N⁺-CH₂CO-phenyl-OAc, OAc, Cl⁻ | 2.3(s,6H); 2.8(s,3H); 6.2(s,2H); 7.5–8.3(m,4H); 8.8(d,1H); 9.36(s,1H) |
| 4 | CH₃S-thiophene-pyridinium-N⁺CH₂CO-phenyl-OAc, OAc, Cl⁻ | 2.1(s,6H); 2.8(s,3H); 6.5(s,2H); 6.8–8.2(m,5H); 9.4(s,1H) |

TABLE 1-continued

| Starting material for Example No(s) | Formula | NMR |
|---|---|---|
| 2,5,9,10,12,13 | 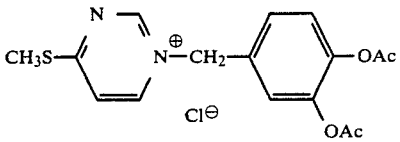 | 2.2(s,6H); 2.7 (s,3H); 5.6(s,2H); 8.1-9(m,5H); 9.6 (s,1H) |
| 6 | 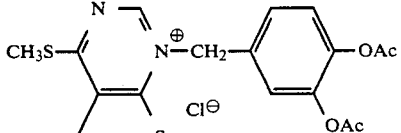 | 2.2(s,6H); 2.8 (s,3H); 6(s,2H); 7.2-7.6(m,3H); 7.7(d,1H); 8.1(d,1H); 9.7(s,1H) |
| 7 | 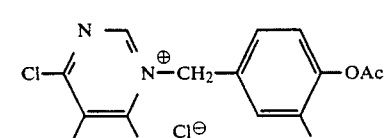 | 2.2(s,6H); 6.1(s,2H); 7.2-8(m,4H); 8.3 (m,2H); 9.4(d,1H) |
| 3,11,14 | 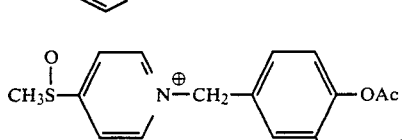 | 2.2(s,6H); 3.4(s,3H); 6(s,2H); 7.2-7.6 (m,3H); 8.6(d,2H); 9.5(d,2H) |

The heterocyclic starting materials for Examples 17-21 were prepared by heating the corresponding diphenylmethyl protected dihydroxy phenyl-4-(1H)pyridone or phenylethyl-4(1H)pyridone at 80° C. for 15 minutes in POCl₃. The reaction mixture was evaporated to dryness, the residue was triturated under ether and the resultant solid collected by filtration and used without further purification.

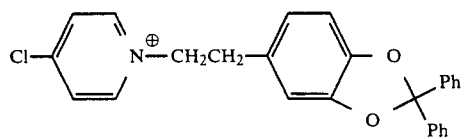

3.2(t,2H); 4.8(t,2H); 6.5-8(m,13H); 8.2(d,2H); 9(d,2H).

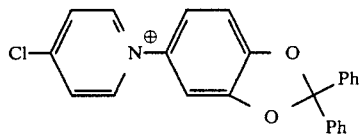

7.3-7.8(m,13H); 8.3-8.6(m,2H); 9.1-9.4(m,2H).

The preparation of the starting material for Examples 23-5

4-Chloropyridine hydrochloride (12.0 g; 80 mmole) was dissolved in water, treated with NaHCO₃ and the aqueous mixture extracted with ether. The ether extracts were dried with MgSO₄, filtered and evaporated to give a residue of 4-chloropyridine. This was dissolved in dry THF (200 ml) and the solution dried over activated molecular sieves (4A). The THF solution was decanted from the sieve, cooled to −60° C. and then treated, under argon, dropwise (keeping the temperature <50° C.) with a THF solution of, 3,4-dimethylmethylenedioxyphenyl magnesium bromide which had been prepared from 3,4-dimethylmethylene dioxybromobenzene (20.2 g, 88 mmole) and magnesium turnings (4 g) in THF (200 ml). When the addition of the Grignard derivative was complete the reaction mixture was immediately treated with phenylchloroformate (10.06 ml, 12.52 g, 80 mmole). After stirring at −50° C. for 15 min. The mixture was allowed to warm up to R.T. and stirred at this temperature for 1 hour before being quenched with aqueous 20% NH₄Cl solution (30 ml). Ether was added and the organic layer was washed with 2NHCl (30 ml), water (2×10 ml) and finally, with brine (2×10 ml).

After drying over MgSO₄, the solution was evaporated to give an oil which was purified by chromatography on silica using hexane:CH₂Cl₂ (3:2) as the eluant. The appropriate fractions were combined and evaporated to give a pale-yellow oil (31.7 g). NMR (CDCl₃): 1.62(s,6H); 5.29(d,1H); 5.65(d,1H); 5.83(d,1H); 6.61(m,1H); 6.7-6.95(m,4H); 7.04(d,1H); 7.15(m,1H); 7.28(m,2H); MS(EI)383M+. The dihydro pyridine (31.5 g) was dissolved in toluene (440 ml) and treated, under argon, with a solution of o-chloranil (19.0 g, 88 mmole) in glacial acetic acid (154 ml). The orange-coloured solution was left at room temperature overnight. The following morning the mixture was concentrated under reduced pressure, the residue dissolved in toluene (300 ml) and extracted with saturated, cold (5° C.), aqueous NaHCO₃ (2×300 ml). The organic phase was then washed with H₂O and brine before being evaporated to give a dark coloured oil (47 g). The oil was extracted several times with hot hexane (3×250 ml), the hexane solution treated with charcoal, filtered, and evaporated to give a residue (17.4 g). This was dissolved in ethyl acetate (100 ml) and ethereal hydrochloric acid added. The desired product, 4-chloro-2-(3',4'-dimethylmethylenedioxyphenyl)pyridine separated as the crystalline HCl salt (6.86 g), mp 153°-8°.

$C_{14}H_{13}Cl_2NO_2 \cdot 1H_2O$ requires C,53.1; H,4.7; N,5.06, Cl, 22.4; $H_2O$ 5.7% found, C, 54.5; H,4.7; N,4.7: Cl, 23.1, $H_2O$, 6.7%. NMR ($d_6$DMSO): 1.71(s,6H); 6.92(d,d,1H); 7.46(d,d,1H); 7.60(d,1H); 7.63(d,d,1H); 8.02(d,1H); 8.59(d,1H); MS(+veFAB) (M+H)+262.

The above hydrochloride (6.5 g) was then heated at 65° C., in dioxan (25 ml) and conc HCl (25 ml), for 2½ hr. The solvent was removed under reduced pressure, the residue dissolved in a mixture of toluene and $CH_3CN$ and the solution again evaporated to dryness under reduced pressure to give 4-chloro-2(3',4'-dihydroxyphenyl)pyridine. The product was then treated with acetic anhydride (25 ml) and pyridine (12 ml) at 70° for 1½ hr. The solvent was removed under reduced pressure, the residue dissolved in $CH_2Cl_2$ (90 ml) and the solution washed with 30% aqueous $NaHCO_3$. The $CH_2Cl_2$ solution was then dried ($MgSO_4$) and evaporated to give the product, 4-chloro-2(3',4'-diacetoxyphenyl)pyridine, as a crystalline solid (5.32 g) m.p 106°-107° C. NMR, $CDCl_3$; 2.32(s,6H); 7.26(dd,1H); 7.32(d,1H); 7.7(d,1H); 7.88(m,2H); 8.58(d,1H).

4-Chloro-2(3',4'-diacetoxyphenyl)pyridine (153 mg; 0.5 mmole) was dissolved in dichloromethane, stirred with activated molecular sieves (4A) for 5 minutes, and then treated with trimethyloxonium tetrafluoroborate (74 mg, 0.5 mmole). The reagent gradually dissolved and after an hour the solution was ready for use. In a parallel reaction in $CDCl_3$ the reaction mixture was examined by NMR to check that the desired reagent had been formed: 2.22(s,3H); 2.26(s,3H); 4.05(s,3H); 7.34(d,1H); 7.4-7.5(m,2H); 7.66(1H,d); 7.84-7.86(d,d,1H); 8.74(d,1H).

Preparation of starting-material for Examples 26 and 27

To a solution of the protected 6,7-dihydroxy-4-methylthioquinazoline (800 mg, 2.3 mmol) in dichloromethane (20 ml) was added trimethyloxonium tetrafluoroborate (340 mg, 2.3 mmole). The mixture was stirred at 20° C. for 4 hours, evaporated, triturated under ether and the solid used without further purification.

Preparation of starting-material for Example 28

A solution of the protected 6,7-dihydroxy-4-chloroquinolone in phosphorus oxychloride was heated at 60° C. for 30 minutes. The reaction mixture was evaporated under reduced pressure and extracted into dichloromethane. The dichloromethane extract was used without any further purification.

Preparation of starting-material for Examples 29 and 30 a) A solution of lithium diisopropylamide was prepared from addition of n-butyllithium (3.95 ml of a 1.53M solution, 6.04 mmole) to diisopropylamine (0.85 ml, 6.04 mmole) in THF (1 ml) at −15° C. After stirring at this temperature for 10 minutes under argon, the reaction was cooled to −75° C., diluted with THF (3 ml) and a solution of 4-methylthiothieno[2,3-d]pyrimidine (1.00 g, 5.49 mmole) in THF (6 ml) added dropwise over 12 minutes. The reaction was warmed to −30° C., cooled again to −75° C. and tri-n-butyltin chloride (1.50 ml, 5.5 mmole) added. Upon warming to room temperature over 30 minutes, the reaction was diluted with ether (60 ml) and washed with water (4×15 ml) then brine (10 ml) before drying over $Na_2SO_4$. Removal of solvent gave a red oil (2.74 g) which was flash chromatographed on a 24 mm diameter silica gel column using 15% diethyl ether/hexane to provide 6-tributylstannyl-4-methylthiothieno[2,3-d]pyrimidine (1.91 g, 67%) as a pale yellow liquid NMR ($CDCl_3$) 0.91(3H,t), 1.20(2H,m), 1.37(2H,m), 1.58(2H,m); 2.71(3H,s); 7.36(1H,s); 8.77(1H,s) m/s 473(M+), 415, 359, 301.

b) The stannane from a) above (1.91 g, 4.05 mmole) was heated to reflux under argon with 3,4-diacetoxybromobenzene (1.11 g, 4.05 mmole) and dichlorobistriphenylphosphine palladium (II) (8.7 mg, 0.5 mol %) in dry THF (10 ml) for 30 hours. The cooled reaction was diluted with ether and the crude product filtered to give 0.34 g. Reduction in volume of the filtrate and precipitation with ether gave a further 0.14 g (32% total yield) of 6-(3,4-diacetoxyphenyl)-4-methylthiothieno[2,3-d]pyrimidine NMR ($CDCl_3$) 2.32(3H,s), 2.34(3H,s), 2.72(3H,s); 7.29(1H,d); 7.45(1H,s); 7.56(1H,dd); 7.59(1H,d) m/s 374(M+),332, 290.

c) The thieno[2,3-d]pyrimidine (0.34 g, 0.91 mmole) was suspended in dry methylene chloride (4 ml) and trimethyloxonium tetrafluoroborate (0.15 g, 1.0 mmole) added with vigorous stirring under argon. After 4 hours, the reaction was triturated with ether and the precipitate filtered to give 0.44 g (102%) of a pale yellow powder which was stored in vacuo. NMR analysis showed this to be 1-methyl-6-(3,4-diacetoxyphenyl)-4-methylthiothieno[3,4-d]pyridinium tetrafluoroborate as a 5:1 mixture with its 2-methyl isomer NMR ($d_6$DMSO) 2.32(3H,s); 2.34(3H,s); 2.90(3H,s), 4.31(3H,s); 7.50(1H,d); 7.93(1H,dd); 8.07(1H,d); 8.38(1H,s); 9.49(1H,s) m/s 398(cation), 347, 305.

Preparation of starting-material for Example 31 a) 6-Tributylstannyl-4-methylthiothieno[2,3-d]pyrimidine (as described above) (1.0 g, 2.12 mmole) in chloroform (2 ml) with 3,4-diisobutyroxybenzoyl chloride (0.64 g, 2.04 mmole) and dichlorobistriphenylphosphine palladium (II) (8 mg, 0.5 mol %) was heated at 65° C. in a sealed tube for 60 hours. The cooled reaction was diluted with chloroform (5 ml), and washed with water (10 ml), saturated aqueous potassium fluoride (2×10 ml) and dried. Removal of solvent and trituration with ether gave 460 mg of a powder which was chromatographed with 25% ether/hexane to give 6-(3,4-diisobutyroxybenzoyl-4-methylthiothieno[2,3-d]pyrimidine (0.17 g, 18%) NMR ($CDCl_3$) 1.30(6H,s); 1.37(6H,s); 2.73(3H,s); 2.81(2H,m); 7.36(1H,d); 7.75(1H,s); 7.79(1H,dd); 7.84(1H,s); 8.84(1H,s) m/s 599(M+H)+.

b) In a similar manner to step c) in the preparation of the starting material for Example 29 1-methyl-6-(3,4-diisobutyroxybenzoyl)-4-methylthiothieno[2,3-d]pyridinium tetrafluoroborate was prepared isomerically pure. NMR ($d_6$DMSO) 1.23(6H,s); 1.31(6H,s); 2.85(2H,m); 2.92(3H,s); 4.34(3H,s); 7.56(1H,d); 7.92(1H,d); 7.98(1H,dd); 8.38(1H,s); 9.55(1H,s).

Preparation of starting material for Example 32

5-Methoxychlorokojic acid (5 mmol) and 4-methylthiopyridine (5.5 mmol) were heated, as an intimate mixture, at 100° C. for 10 minutes. A brown glass formed which crystallised on trituration with dichloromethane to give 1-(5-methoxypyran-4-on-2-yl)-4-methylthiopyridinium chloride (67%, after recrystallisation from isopropanol); (DMSO-$d_6$) 2.72(s,3H);

3.63(s,3H); 5.80(s,2H); 6.65(s,1H); 8.00(s,1H); 8.12(d,2H); 8.95(d,2H).

To a stirred suspension of this pyridinium chloride (1 mmol) in dichloromethane (5 ml) at 0° C. was added sufficient trifluoroacetic acid to give a clear solution. A solution of m-chloroperoxybenzoic acid (1 mmol) in dichloromethane (2 ml) was added over about 1 minute and the mixture was allowed to warm to room temperature. After 30 minutes, further m-chloroperoxybenzoic acid (1 mmol) in dichloromethane (2 ml) was added. After a further 15 minutes the solvent was removed by evaporation under reduced pressure and the residue was triturated with ethyl acetate to give 1-(5-methoxypyran-4-on-2-yl)4-methylsulphinylpyridinium chloride as a crude gum (which was used in this form for the reaction of Example 32); (DMSO-d$_6$) 3.00(s,3H); 3.65(s,3H); 6.0(s,2H); 6.70(s,1H); 8.15(s,1H); 8.55(d,2H); 9.42(d,2H).

Preparation of starting material for Example 33

Chlorokojic acid (5 mmol) and 4-methylthiopyrimidine (5 mmol) were stirred at 170° C. for 10 minutes. The mixture melted, turned black, resolidified and was triturated with acetone to give as a crude solid, 1-(5-hydroxypyran-4-on-2-yl)-4-methylthiopyrimidinium chloride hydrochloride salt; (DMSO-d$_6$)/130° C., 2.80(s,3H); 5.79(s,2H); 6.65(s,1H); 8.08(s,1H); 8.15(q,1H); 9.05(q,1H); 9.65(s,1H).

Preparation of starting material for Examples 34–35

2-Chloromethyl-4,5-dihydroxypyridine (1.5 mmol) and 4-methylthiopyrimidine (3 mmol) were heated at 100° C., under argon, for 30 minutes. The mixture was subsequently triturated with methanol at 0° C., filtered, washed and dried to give 1-(4,5-dihydroxypyridin-2-ylmethyl)-4-methylthiopyrimidinium chloride hydrochloride; (DMSO-d$_6$) 2.75(s,3H); 5.90(s,2H); 7.45(s,1H); 8.15(s,1H); 8.17(q,1H); 9.05(q,1H); 9.75(s,1H).

Preparation of starting material for Example 36

2-Chloroacetyl-4,5-dibenzyloxypyridine (0.92 mmol) in hydrochloric acid/acetic acid (5 ml) was heated at reflux for 4½ hours in a stream of hydrogen chloride. The solution was filtered whilst hot and on cooling 2-chloroacetyl-4,5-dihydroxypyridine crystallised; (DMSO-d$_6$) 5.15(s,2H); 7.55(s,1H); 8.08(s,1H).

The above pyridine (0.71 mmol) and 4-methylthiopyrimidine (1.42 mmol) were stirred at 100° C. for 15 minutes. The viscous mixture was triturated to give, as a residue, 1-(4,5-dihydroxypyridin-2-ylcarbonylmethyl)-4-methylthiopyrimidinium chloride hydrochloride which was used directly in Example 36.

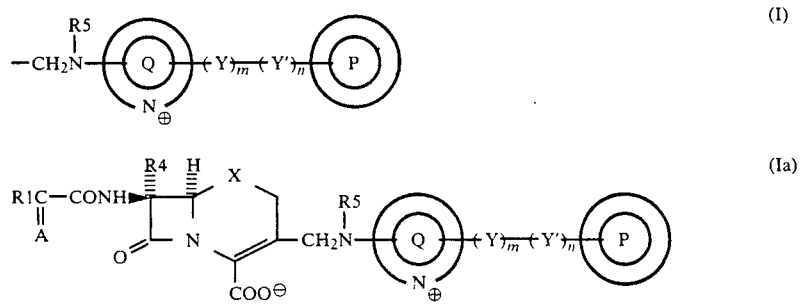

(I)

(Ia)

(II)

(III)

(IV)

(V)

(VI)

-continued
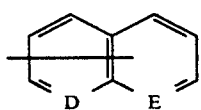 (VII)
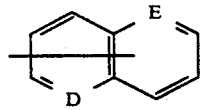 (VIII)
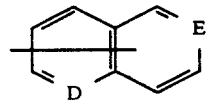 (IX)
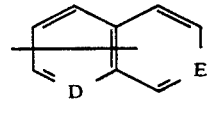 (X)
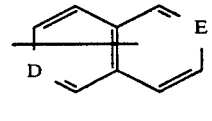 (XI)
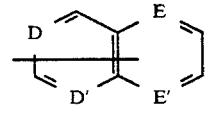 (XII)
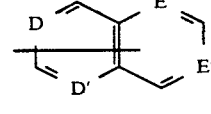 (XIII)
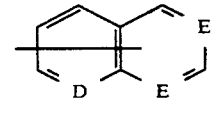 (XIV)
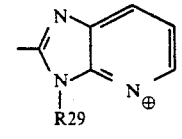 (XV)
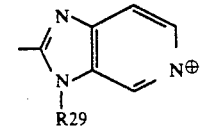 (XVI)
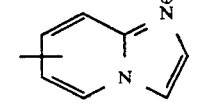 (XVII)
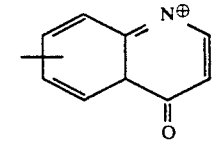 (XVIII)

-continued
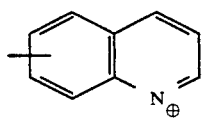 (XIX)
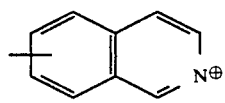 (XX)
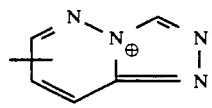 (XXI)
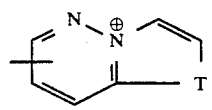 (XXII)
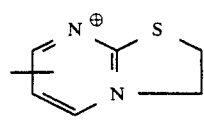 (XXIII)
==== = Single or double bond
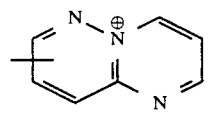 (XXIV)
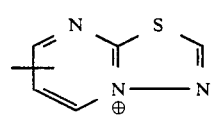 (XXV)
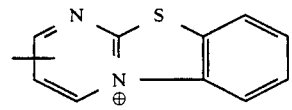 (XXVI)
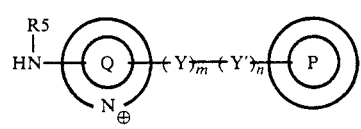 (XXVII)
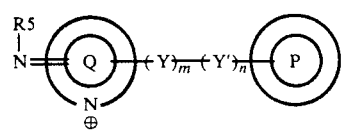 (XXVIII)
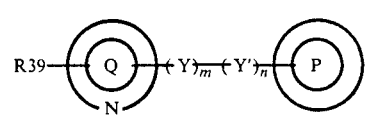 (XXIX)
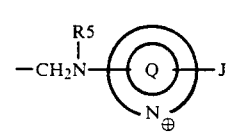 (XXX)
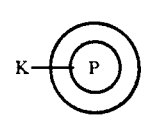 (XXXI)

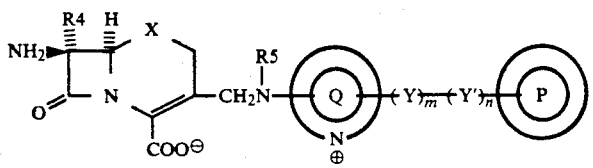 (XXXII)

 (XXXIII)

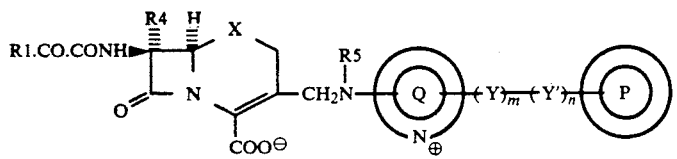 (XXXIV)

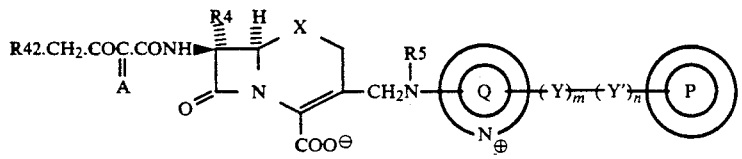 (XXXV)

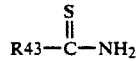 XXXVI

We claim:

1. A cephalosporin compound of the formula (Ia):

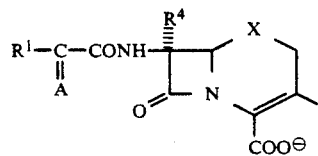

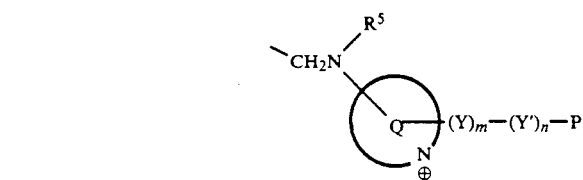

wherein:

X is sulphur or sulphinyl;

$R^1$ is 2-aminothiazol-4-yl or aminooxazol-4-yl each optionally substituted in the 5-position by fluorine, chlorine or bromine, or R1 is 5-aminoisothiazol-3-yl, 5-amino-1,2,4-thiadizol-3-yl, 3-aminopyrazol-5-yl, 3-aminopyrazol-4-yl, 2-aminopyrimidin-5-yl, 2-aminopyrid-6-yl, 4-aminopyrimidin-2-yl, 2-amino-1,3,4-thiadiazol-5-yl or 5-amino-1-methyl-1,2,4-triazol-3-yl;

A is of the formula =NOR² (having syn configuration about the double bond) wherein R2 is hydrogen, (1–6C)alkyl, (3–8C)cycloalkyl, (1–3C)alkyl(3–6C)cycloalkyl) (3–6C)cycloalkyl(1–3C)alkyl, (3–6C)alkenyl, optionally substituted by carboxy, (5–8C)cycloalkenyl, (3–6C)-alkynyl, 2–5C)alkylcarbamoyl, phenylcarbamoyl, benzycarbamoyl, di-(1–4C)alkylcarbamoyl(1–4C)alkyl, 1–4C)haloalkylcarbamoyl(-1–4C)alkyl, (1–3C)haloalkyl, 2–6C)hydroxyalkyl, (1–4C)alkoxy(2–4C)alkyl, (1–4C)alkylthio(2–4C)alkyl, 1–4C)alkanesulphinyl(1–4C)alkyl, (1–4C)alkanesulphonyl(1–4C)alkyl, amino(2–6C)alkyl, azido(-2–6C)alkyl, ureido(C2-6)alkyl, (1–4C)alkylamino(1-6C)alkyl, (2–8C)dialkylamino(2–6C)alkyl, 1–5C)cyanoalkyl, 3-amino-3-carboxypropyl, 2-(amidino)ethyl, 2-(amidinothio)ethyl, 2-(N-aminoamidinothio)ethyl, tetrahydropyran-2-yl, thietan-3-yl, 2-oxopyrrolidinyl, or 2-oxotetrahydrofuranyl, or —R2 is of the formula IV

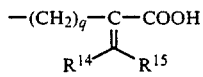

in which q is 1 or 2 and R14 and R15 are hydrogen or (1–4C)alkyl or —R2 is of the formula V

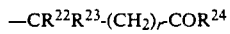

in which r is 0–3, R22 is hydrogen, (1–3C)alkyl or methyltio, R23 is hydrogen, (1–3C)alkyl, (3–7C)cycloalkyl, cyano, carboxy, (2–5C)carboxyalkyl or methanesulphonylamino, or R22 and R23 are joined to form, together with the carbon to which they are attached, a (3–7C)-carbocyclic ring, and R24 is hydroxy, amino, (1–4C)alkoxy, (1–4C)alkylamino or of the formula NHOR25 in which R25 is hydrogen or (1–4C)alkyl:

or A may be of the formula =CH.R3 wherein R3 is hydrogen, halogen, (1–6C)alkyl, (3–7C)cycloalkyl, (2–6C)alkenyl, (3–7C)cycloalkenyl, phenyl or benzyl;

R⁴ is hydrogen, methoxy or formamido;

R⁵ is hydrogen, (1–4C)alkyl, halo(1–4C)alkyl, hydroxy(1–4C)alkyl, (1–4C carboxy(l-4C)alkyl, amino(1–4C)alkyl, cyano(1–4C)alkyl, (1–4C)alkanoylamino(-1–4C)alkyl, (3–6C)alkenyl, phenyl(1–4C)alkyl or heteroaryl(1–4C)alkyl wherein heteroaryl is furan or 4-pyridyl;

Q is a 5 or 6 membered ring containing the positively charged nitrogen atom and 0 to 3 further hetero atoms selected from nitrogen, oxygen and sulphur optionally fused on an available carbon-carbon or carbon-nitrogen bond to a benzene ring or a ring of the formula (VI):

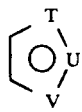
(VI)

wherein T, U and V are selected from oxygen, sulphur, nitrogen, carbon, —NH— and —CH—;
or ring Q is of the formula VII-XXVI:

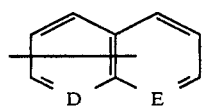
(VII)

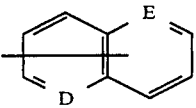
(VIII)

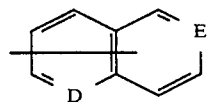
(IX)

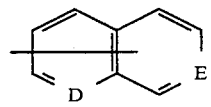
(X)

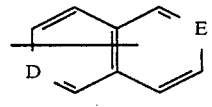
(XI)

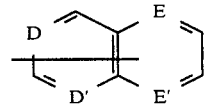
(XII)

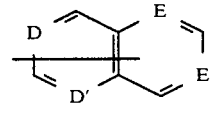
(XIII)

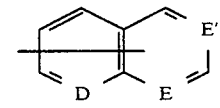
(XIV)

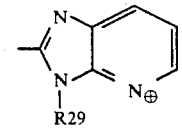
(XV)

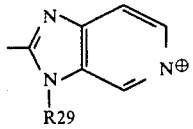
(XVI)

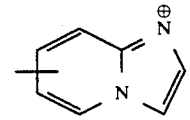
(XVII)

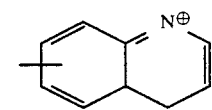
(XVIII)

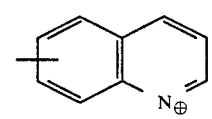
(XIX)

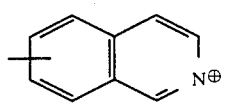
(XX)

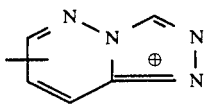
(XXI)

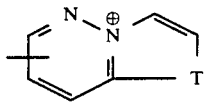
(XXII)

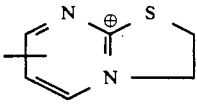
(XXIII)

=== = Single or double bond

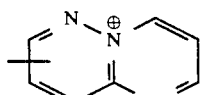
(XXIV)

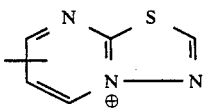
(XXV)

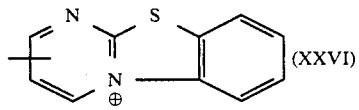
(XXVI)

wherein D, D$^1$, E and E$^1$ represent nitrogen atoms one of which bears a positive charge and R$^{29}$ is hydrogen or a group R$^{27}$ (as hereinafter defined);
ring Q and the rings VI-XXVI being optionally substituted by at least one group R$^{26}$, R$^{27}$ or R$^{30}$ (as hereinafter defined);
on a carbon atom or atoms available for substitution by 1,2 or 3 groups R26 wherein R26 is halogen, (1-6C)alkyl, carboxy, (2-6C)alkoxycarbonyl, (2-6C)-alkoxycarbonyl(1-4C)alkyl, (1-6C)alkoxy, (1-6C)alkylthio, cyano, (1-4C) cyanoalkyl, amino, (1-6C)alkylamino, (2-8C)dialkylamino, phenyl(1-4C)alkylamino, nitrophenyl(1-4C)alkylamino, (3-6C)alkeynlamino, amino(1-6C)alkylamino, (1-6C)alkoxy(-1-6C)alkylamino, hydroxy(1-6C)alkylamino, hydroxy, mercapto, carbamoyl, (2-6C)alkylcarbamoyl, (3-10C)dialkylcarbamoyl, phenylthio and heteroarylthio (wherein heteroaryl is furan, thiophene, imidazole, thiazle, pyrazole, thiadiazole, pyridine, pyrimidine, pyrazine or pyridazine) wherein when more than one group R26 is present these may be the same or different;
on an uncharged nitrogen atom available for substitution by a group R27 wherein R27 is (1-6C)alkyl, phenyl or benzyl;
on the charged nitrogen atom where possible by a group R30 wherein R30 is hydrogen, (1-6C)alkyl (optionally substituted by carboxy, (1-6C)alkoxycarbonyl, carbamoyl, mono-or di-(1-4C)alkylcarbamoyl, hydroxy, (1-4C)alkoxy, amino, mono-or di-(1-4C)alkylamino, (1-4C)alkanoyl, benzoyl, cyano, carboxyaminocarbonyl, (1-6C)alkoxycarbonylaminocarbonyl, (1-4C)alkoxy(2-4C)alkoxy or phenyl), (1-6C)alkoxy, phenyl(1-6C)alkoxy, amino, (1-6C)alkylamino, (3-6C)cycloalkyl, (3-6C)cycloalkenyl, cyano(3-6C)cycloalkenyl, (2-6C)alkenyl (optionally substituted by (1-6C)alkyl, halogen, cyano, carbamoyl, mono-or di-(1-4C)alkylcarbamoyl, piperidinocarbonyl or morpholinocarbonyl), 2-ureidoethyl, 2-thioureidoethyl, 2-(thioacetylamino)et sulphamoyl, 2-amino-2-carboxyethyl, acetylaminomethyl, phthalimidomethyl, 4-5-dihydromidazol-2-yl-methyl, 3,4,5,6-tetrahydropyrimidin-2-ylmethyl, 2-(1,2,3,6-tetrahydro-2,6-dioxopurin-7-ylethyl, 2-hydroxyiminiopropyl (syn or anti) (1-4C)alkoxyimino propyl (syn or anti) or phenyl, or R30 is of the formula —$(CH_2)_2$-NR31R32R33 in which R31, R32 and R33 are (1-4C)alkyl, or R30 is of the formula —$(CH_2)_s$-R34 in which s is 0-2 and R34 is pyridine, pyridazine, pyrimidine, pyrazine, 1,2,5,6-dihydro-5,6-dioxo-1,2,4-triazine, 2-(1-4C)alkyl-1,2,5,6-dihydro-5,6-dihydro-5,6-dioxo-1,2,4-triazine, 1-[(1-4C)-alkyl]tetrazole, furan, thiophene, pyrrole, 1-(1-4C)alkyl-pyrrole, oxazole, thiazole, imidazole, 1-(1-4C)alkyl imidazole, isoxazole, isothiazole, pyrazole, 1,2,3-thiadiazole, 1-(1-4C)alkylpyrazole, benzfuran, benzthiophene, indole, oxindole, 1-(1-4C)alkyl indole, benzoxazole, benzthiazole, benzimidazole, 1-(1-4C)alkyl benzimidazole, or 3,4-dihydro-4-oxo-2H-benzo[e]oxazine (each of these ring systems being linked to $(CH_2)_s$ through carbon and each ring system being optionally substituted by halogen, (1-6C)alkyl, (1-4C)haloalkyl, (3-6C)-cycloalkyl, (3-6C)cycloalkyl(1 (2-6C)alkenyl, carboxy, (2-6C)alkoxycarbonyl, (1-6C)alkoxy, cyano, (2-6C)-cyanoalkenyl, carbamoyl, mono-or di-(1-4C)alkylcarbamoyl, (1-4C)alkanoylamino, guanidino, hydroxy, nitro or amino), or R30 is 2-guanidino-thiazol-4-ylmethyl, hydroxybenzoylmethyl, 2-thenyl, 2-imidazolylmethyl or cinnamyl (each optionally substituted by halogen, (1-6C)alkyl, hydroxy, (1-4C)alkoxy, carboxy, (2-6C)alkoxycarbonyl, nitro or carbamoyl), or R30 is —$(CH_2)_t$NHCOR35 or —$(CH_2)_t$S(O)u-R35 in which t is 1-6, u is 0, 1 or 2 and R35 is (1-6C)alkyl or (106C)alkoxy, or R30 is of the formula $(CH_2)_2$N=CR36NR37R38 or —$(CH_2)_v$C(=NR36)NR37R38 or a tautomer thereof in which y is 1-6 and R36, R37, R38 are hydrogen or (1-4C)alkyl, (wherein when R30 is or contains a phenyl group, the phenyl group is optionally substituted by 1 or 2 groups selected from halogen, (1-6C)alkyl, (1-6C)alkoxy, amino, carboxy, nitro, carbamoyl, cyano, trifluoromethyl, aminoethyl, (1-4C)alkonyl, (1-4C)alkanoylamino, halo(1-4C)alkyl, (2-6C)alkoxycarbonyl, mono- or di-(1-4C)alkylcarbamoyl, mesyl, vinyl, sulpho, sulphamoyl or mono or di(1-4C)alkylsulphamoyl);

Y is straight or branched (1-6C)alkylene optionally substituted by cyano, carboxy, (1-4C)alkoxycarbonyl, nitro, halogen, carbamoyl, mono-or di(1-4C)alkylcarbamoyl or trifluoromethyl;

Y' is —CO—, —NHCO—, —CONH—, —NHSO$_2$—, -SO$_2$NH—, —)—, —S—, —CH=CH— or —NR$^a$— wherein Ra is hydrogen, (1-4C)alkyl or (2-4C) alkenyl;

m and n are each 0 or 1, the link between ring Q and the group —$(Y)_m$-$(Y')_n$-P being via an available site on ring Q selected from the positively charged nitrogen atom, an uncharged nitrogen atom or a carbon atom such that when m=0 and n=0 the rings Q and P are linked directly by a covalent bond or are fused on available carbon-carbon or carbon-nitrogen bonds;

P represents:

(i) a benzene ring optionally fused to a further benzene ring (so forming a naphthyl group) and said ring system substituted by groups w and Z which are ortho with respect to one another wherein W is hydroxy or an in vivo hydrolysable ester thereof and Z is hydroxy or an in vivo hydrolysable ester thereof;

ring system P optionally being further substituted by (1-4C)alkyl, halogen, hydroxy, cyano, trifluoromethyl, nitro, amino, mono- or di(1-4C)alkylamino, formyl, (1-4C)alkanoyl, (1-4C)alkoxy, (1-4C)alkylthio, (1-4C)alkanoyloxy, carbamoyl or mono- or di(1-4C)alkylcarbamoy;

and the N-oxides thereof where chemically possible; and pharmaceutically acceptable salts thereof.

2. A compound according to claim 1 wherein ring Q is a pyridine or pyrimidine ring or a pyridine or pyrimidine ring fused to either a benzene ring or thienyl group.

3. A compound according to claim 1 wherein X is sulphur and R$^4$ is hydrogen.

4. A compound according to claim 1 wherein R$^1$ is 2-aminothiazol-4-yl and A is a group =NOR$^2$ wherein R$^2$ is C$_{1-6}$ alkyl, 1-carboxy(C3-7)cycloalkyl or 2-carboxyprop-2-yl.

5. A compound according to claim 1 wherein R$^5$ is hydrogen or C$_{1-4}$ alkyl.

6. A compound according to claim 1 wherein —$(Y)_m$-$(Y')_n$- is substituted on the positively charged nitrogen atom of ring Q and is a direct bond, —CH$_2$—, —CH$_2$CH$_2$— or —CH$_2$CH$_2$NHCO—.

7. An antibacterial pharmaceutical composition which comprises an antibacterially effective amount of a compound according to claim 1 and a pharmaceutically acceptable carrier.

8. A method of treating a bacterial infection in a mammal comprising administering to a mammal in need of such treatment an antibacterially effective amount of a compound according to claim 1.

* * * * *